US011033643B2

(12) United States Patent
Starkweather et al.

(10) Patent No.: US 11,033,643 B2
(45) Date of Patent: Jun. 15, 2021

(54) SYSTEM FOR DISINFECTING LARGER SCALE SPACES AND EQUIPMENT

(71) Applicant: UV-Concepts Inc., Englewood, CO (US)

(72) Inventors: Jeremy Starkweather, Castle Rock, CO (US); Jason Ylizarde, Conroe, TX (US); John Wynne, Cincinnati, OH (US); Pat Hilt, Rancho Cucamonga, CA (US); Thomas Taylor, Yorba Linda, CA (US)

(73) Assignee: UV-Concepts Inc., Englewood, CO (US)

( * ) Notice: Subject to any disclaimer, the term of this patent is extended or adjusted under 35 U.S.C. 154(b) by 0 days.

(21) Appl. No.: 16/390,536

(22) Filed: Apr. 22, 2019

(65) Prior Publication Data
US 2020/0078480 A1 Mar. 12, 2020

Related U.S. Application Data

(62) Division of application No. 15/602,771, filed on May 23, 2017, now Pat. No. 10,272,167.

(60) Provisional application No. 62/398,840, filed on Sep. 23, 2016, provisional application No. 62/340,553, filed on May 24, 2016, provisional application No. 62/340,554, filed on May 24, 2016.

(51) Int. Cl.
*A61L 2/10* (2006.01)
*A61L 2/24* (2006.01)

(52) U.S. Cl.
CPC ............ *A61L 2/10* (2013.01); *A61L 2/24* (2013.01); *A61L 2202/11* (2013.01); *A61L 2202/122* (2013.01); *A61L 2202/14* (2013.01); *A61L 2202/16* (2013.01); *A61L 2202/24* (2013.01); *A61L 2202/25* (2013.01)

(58) Field of Classification Search
CPC ........ A61L 2/00; A61L 2/0029; A61L 2/0047; A61L 2/02; A61L 2/08; A61L 2/10
USPC .................. 250/492.1, 493.1, 453.11, 455.11
See application file for complete search history.

(56) References Cited

U.S. PATENT DOCUMENTS

| 2,375,226 A | 5/1945 | Higgins |
| 4,743,059 A | 5/1988 | Legueu |

(Continued)

FOREIGN PATENT DOCUMENTS

| CN | 102266166 A | 12/2011 |
| EP | 0755271 B1 | 1/2002 |

(Continued)

OTHER PUBLICATIONS

Office Action for U.S. Appl. No. 15/602,771, dated Aug. 31, 2018, 11 pages.

(Continued)

*Primary Examiner* — Jason L McCormack

(57) ABSTRACT

The present disclosure relates generally to systems, devices and methods for disinfection of space and equipment. In particular, the present disclosure relates to systems, devices and methods, such as rolling enclosures, which use light sources, such as ultraviolet (UV) light, and more specifically UV-C light, to disinfect larger scale equipment or spaces. Systems and methods of the present disclosure are particularly useful in medical facilities for treating medical equipment or spaces, where the prevalence of pathogens requires frequent disinfecting.

21 Claims, 21 Drawing Sheets

(56) References Cited

U.S. PATENT DOCUMENTS

| | | | |
|---|---|---|---|
| 4,877,964 | A | 10/1989 | Tanaka et al. |
| 5,597,597 | A | 1/1997 | Newman |
| 5,958,336 | A | 9/1999 | Duarte |
| 6,165,526 | A | 12/2000 | Newman |
| 6,649,921 | B1 | 11/2003 | Cekic et al. |
| 6,730,923 | B1 | 5/2004 | May et al. |
| 7,490,578 | B1 | 2/2009 | Mottard |
| 7,791,044 | B1 | 9/2010 | Taylor et al. |
| 7,829,016 | B2 | 11/2010 | Deal et al. |
| 8,067,750 | B2 | 11/2011 | Deal |
| 8,536,541 | B2 | 9/2013 | Taylor et al. |
| 9,107,973 | B1* | 8/2015 | Robinson .............. A61L 2/22 |
| 9,492,577 | B1 | 11/2016 | Dayton |
| 9,682,161 | B2 | 6/2017 | Farren et al. |
| 9,687,575 | B2 | 6/2017 | Farren |
| 9,707,306 | B2 | 7/2017 | Farren |
| 10,046,073 | B2 | 8/2018 | Farren et al. |
| 10,255,466 | B2 | 4/2019 | Jinedatha |
| 10,272,167 | B2 | 4/2019 | Starkweather et al. |
| 10,603,394 | B2 | 3/2020 | Farren et al. |
| 2002/0104271 | A1 | 8/2002 | Gallant |
| 2002/0168287 | A1 | 11/2002 | Eckhardt et al. |
| 2003/0133834 | A1 | 7/2003 | Karle |
| 2004/0052702 | A1 | 3/2004 | Shuman et al. |
| 2004/0170525 | A1 | 9/2004 | Ettlinger et al. |
| 2005/0063815 | A1 | 3/2005 | Pierson et al. |
| 2005/0201910 | A1 | 9/2005 | Shou et al. |
| 2006/0104858 | A1 | 5/2006 | Potember et al. |
| 2006/0186358 | A1 | 8/2006 | Couvillion |
| 2007/0012340 | A1 | 1/2007 | Jones et al. |
| 2008/0008620 | A1 | 1/2008 | Alexiadis |
| 2010/0007492 | A1 | 1/2010 | Ressler et al. |
| 2011/0073774 | A1* | 3/2011 | Taylor .............. A61L 2/10 250/492.1 |
| 2011/0274581 | A1 | 11/2011 | Davis |
| 2012/0062366 | A1 | 3/2012 | Pappu et al. |
| 2012/0181447 | A1 | 7/2012 | Yerby |
| 2012/0280147 | A1* | 11/2012 | Douglas ............ A61L 2/10 250/492.1 |
| 2013/0175460 | A1 | 7/2013 | Farren |
| 2013/0216438 | A1 | 8/2013 | Hill et al. |
| 2013/0256560 | A1* | 10/2013 | Yerby .............. A61L 2/10 250/455.11 |
| 2014/0291552 | A1* | 10/2014 | Schumacher ........... A47L 25/04 250/492.1 |
| 2014/0319375 | A1* | 10/2014 | Nelson .............. A61L 2/025 250/455.11 |
| 2015/0118107 | A1* | 4/2015 | Sunkara ............ A61B 90/98 422/24 |
| 2015/0367008 | A1 | 12/2015 | Romo et al. |
| 2017/0049915 | A1* | 2/2017 | Brais ............... H05B 47/105 |
| 2017/0260681 | A1* | 9/2017 | Gao ............... A61L 2/00 |
| 2018/0140727 | A1 | 5/2018 | Romo et al. |
| 2019/0347451 | A1 | 11/2019 | Jinedatha |
| 2020/0254122 | A1 | 8/2020 | Starkweather et al. |

FOREIGN PATENT DOCUMENTS

| | | |
|---|---|---|
| IT | AT20120001 U1 | 11/2013 |
| WO | WO 2015167614 | 11/2015 |

OTHER PUBLICATIONS

Office Action for U.S. Appl. No. 15/602,771, dated Mar. 16, 2018, 9 pages.

International Search Report and Written Opinion for International Application No. PCT/US2017/033996, dated Nov. 15, 2017, 17 pages.

International Search Report and Written Opinion for International Application No. PCT/US2019/038231, dated Oct. 18, 2019, 12 pages.

Boyce, J. M., "Modern technologies for improving cleaning and disinfection of environmental surfaces in hospitals," Boyce Antimicrobial Resistance and Infection Control (2016) 5:10, 10 pages.

Sarwar, A. T. M. G. et al., "Semiconductor Nanowire Light Emitting Diodes Grown on Metal: A Direction Towards Large Scale Fabrication of Nanowire Devices," Department of Electrical and Computer Engineering, The Ohio State University, 2015, 18 pages.

May, B. J. et al., "Nanowire LEDs Grown Directly on Flexible Metal Foil," Department of Electrical and Computer Engineering, The Ohio State University, 2016, 15 pages.

Myers, R. C. et al., "Ultraviolent Nanowire LEDs Grown Directly on Flexible Metal Foil," The Ohio State University Accelerator Award Presentation, Jul. 11, 2017, 6 pages.

Ma, X. et al., "RFID-Based Healthcare Workflow Management in Sterile Processing Departments," Proceedings of the 2012 Industrial and Systems Engineering Research Conference (2012), 11 pages.

Infection Control Today, "Technology Aids in HAI Prevention," [Online], Retrieved from the Internet: <URL: https://www.infectioncontroltoday.com/hand-hygiene/technology-aids-hai-prevention>, Jul. 23, 2009, 11 pages.

Yedidia, "Tag Archive for asset tracking," in Medical Devices and Technology, Bob on Medical Device Software, [Online], Retrieved from the Internet: <URL: http://bobonmedicaldevicesoftware.com/blog/tag/asset-tracking/>, Oct. 25, 2011, 5 pages.

Xu, S. et al., "A RFID-based tracking system of endoscopes," 2011 4th International Conference on Biomedical Engineering and Informatics (BMEI), IEEE Xplore Digital Library [Online], <URL:https://ieeexplore.ieee.org/document/6098686>, Oct. 15-17, 2011, Shanghai, China.

Seal Shield, "ElectroClave UV-C Disinfection with Mobile Device Management—SSECLAVE4B," [Online], Retrieved from the Internet: <URL: http://www.sealshield.com/Products/Device-Management/ElectroClave-UV-Disinfection-Device-Manager.html>, 2019, 4 pages.

Swedberg, C., "RFID Enables Use of Non-synthetic Cleaner by Tracking Expirations," RFID Journal [Online], Retrieved from the Internet: <URL:https://www.rfidjournal.com/articles/view?17574>, Jun. 2018, 3 pages.

Nanosonics, "trophon2 Consumables and Accessories," [Online], Retrieved from the Internet: <https://www.nanosonics.com.au/trophon2-consumables-and-accessories/>, 2017, 9 pages.

Inahta Brief, "The clinical value of ultraviolet rays UV-C used for disinfection of endocavitary ultrasonography probes," Issue 2015/002 [Online], Retrieved from the Internet: <URL: http://www.inahta.org/upload/2015/15002_Antigermix.pdf>, 2015, 1 page.

Olympus, "Meet the demands of your busy schedule with the OER-Pro. 99% Uptime," [Online], Retrieved from the Internet: <URL:https://medical.olympusamerica.com/customer-resources/cleaning-disinfection-sterilization/reprocessing-products/oer-pro>, 2020, 6 pages.

Quake Global, "Medical Equipment Management," [Online], Retrieved from the Internet: <URL: https://www.quakeglobal.com/healthcare-rfid-equipment-management-processes>, 2019, 3 pages.

Pletersek, A. et al., "Monitoring, Control and Diagnostics using RFID Infrastructure," J. Med. Syst. (2012) 36:3733-3739.

International Search Report and Written Opinion for International Application No. PCT/US2010/050837, dated Oct. 22, 2010, 7 pages.

First Office Action for Chinese Application No. 201780042406.8, dated Sep. 25 2020, 21 pages.

Office Action for European Application No. 17728013.8, dated Aug. 14, 2020, 6 pages.

Office Action for U.S. Appl. No. 16/860,141, dated Jun. 24, 2020, 13 pages.

Office Action for U.S. Appl. No. 16/860,141, dated Dec. 16, 2020, 10 pages.

* cited by examiner

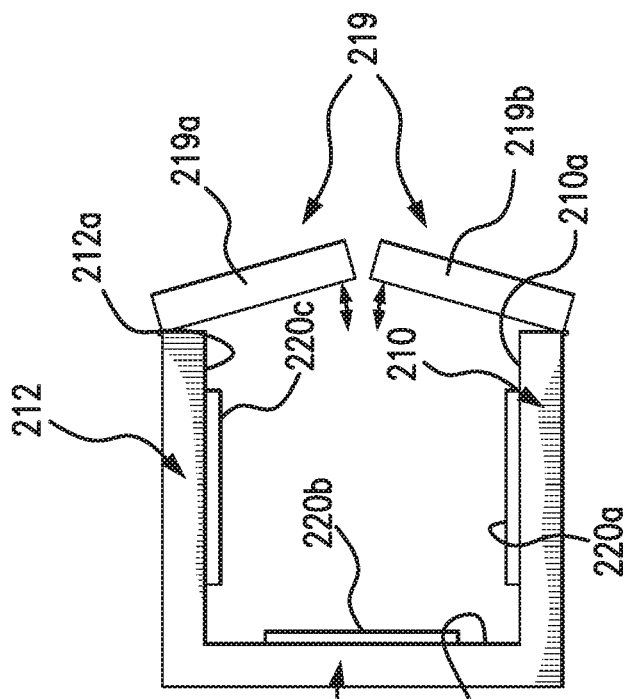
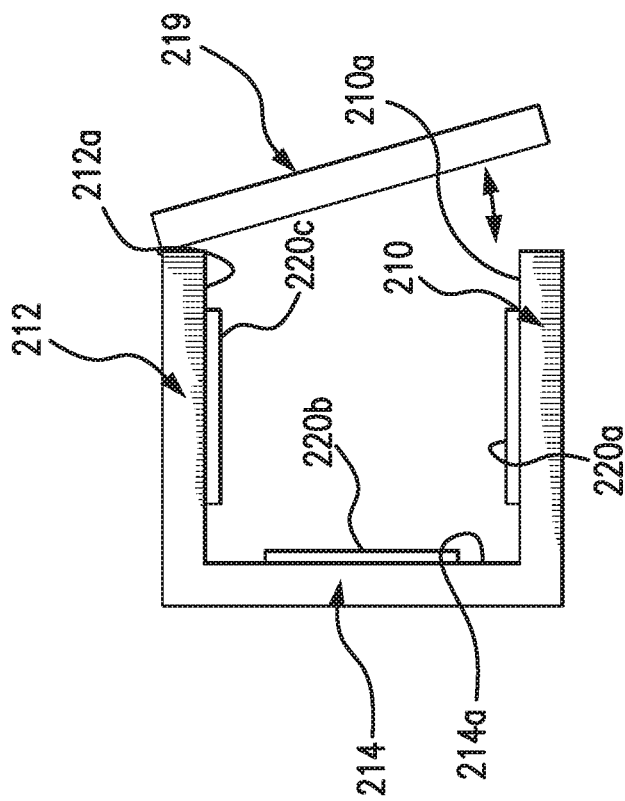
FIG. 3A
FIG. 3B

SYSTEM FOR DISINFECTING LARGER SCALE SPACES AND EQUIPMENT

CROSS REFERENCE TO RELATED APPLICATIONS

This application is a divisional of U.S. patent application Ser. No. 15/602,771, filed May 23, 2017, which claims the benefit of priority under 35 U.S.C. § 119(e) to U.S. Provisional Application Ser. No. 62/340,553, filed May 24, 2016; U.S. Provisional Application 62/340,554, filed May 24, 2016; and U.S. Provisional Application Ser. No. 62/398,840, filed Sep. 23, 2016. The disclosures of each of which are herein incorporated by reference in their entirety.

FIELD

The present disclosure relates generally to systems, devices and methods for disinfection of space and equipment. In particular, the present disclosure relates to enclosures which use energy sources, such as ultraviolet (UV) light, and more specifically UV-C light, to disinfect larger scale equipment. Systems and methods of the present disclosure are particularly useful in medical facilities for treating medical equipment, where the prevalence of pathogens requires frequent disinfecting.

BACKGROUND

The use of ultraviolet (UV) light to disinfect equipment and spaces to reduce the transmission of pathogens between individuals is known. For example, UV light is used to disinfect medical equipment and/or rooms within a hospital to reduce the risk of infection for an already unhealthy patient population.

UV disinfection stations for disinfecting publicly-used equipment are described by Taylor et al. in U.S. Pat. Nos. 7,791,044 and 8,536,541, the disclosures of which are hereby incorporated by reference in their entirety. The stationary units described in these patents are particularly useful for disinfecting mobile equipment, such as shopping carts, wheelchairs, gurneys, etc. Such enclosures, however, are somewhat limited in the range of automation and design features that could improve mobility, accessibility, usage, safety, tracking, productivity and efficiency, among other features. Similarly, UV room disinfection units provide an effective supplemental disinfection means, and have the potential of being an effective primary means of reducing pathogen burden on equipment and/or within spaces.

It has been shown that intensity, proximity and line of sight are critical to the ability of UV light emitted from a disinfection system to effectively eliminate pathogens on equipment and/or within spaces. Commercially available "whole room" UV-C disinfection units, however, are limited in their effectiveness because the units are stationary. To overcome this limitation and effectively reduce pathogen burden throughout the "target area," existing units must be moved manually throughout the room, or multiple units used simultaneously. This limitation can potentially require multiple disinfection cycles and prolong the disinfection process. These units are therefore similarly hampered in the range of available automation and design features that could improve mobility, accessibility, usage, safety, tracking, productivity and efficiency, among other features.

A variety of advantageous medical outcomes may therefore be realized by the systems and/or methods of the present disclosure, which emit UV light with the combined benefits of intensity, proximity and line of sight to efficiently contact and effectively disinfect equipment and/or spaces.

SUMMARY

In one aspect, the present disclosure relates to systems and methods for disinfecting that provide and offer added functionality and design capability, to improve upon disinfecting capabilities, mobility, access, safety, efficiency and productivity, tracking, etc.

In one aspect, the present disclosure relates to portable disinfection systems that are more efficacious for use in addressing stationary or cumbersomely large equipment. Such systems may be enclosed systems with light sources on the interior directing light inward, or may be open systems with light sources on the exterior directing light outward. Light sources, such as arrays of UV-C tubes or LEDs, on the interior or exterior of such mobile units, in various arrangements and configurations, are described more fully herein.

In another aspect, the present disclosure relates to robotic units that are capable of moving through a "target area" or enclosure autonomously by using, e.g., preset waypoints, a roaming mode based on preset sensors in the "target area" or by using integrated sensors on the unit, or by combining one or more of these means, as described more fully herein. The ability to autonomously move through a "target area" places the ultraviolet rays closer to the target pathogens, the proximity and intensity of which may lend to a more effective kill rate of pathogens and may likewise eliminate the need for the unit to be manually placed in other positions by the operator or the need for multiple units, potentially reducing the treatment procedure time.

In another aspect, the present disclosure relates to a disinfection system comprising a chamber that includes a first side wall, a second side wall and a back wall defining an interior. An inner surface of each of the first side wall, second side wall and back wall may include at least one reflective unit. At least one energy source may be housed within each reflective unit. A plurality of rolling elements may be disposed about a bottom portion of the chamber. The first and second side walls may extend substantially perpendicular from opposite sides of the back wall. Each reflective unit may face into the interior of the chamber. Each reflective unit may define a substantially concave shape. Each energy source may be housed within each reflective unit such that energy emitted from the energy source is directed into the interior of the chamber. Each energy source may include an ultraviolet light source. Each ultraviolet light source may be configured to emit ultraviolet energy at an intensity of at least $100\,\mu W/cm^2$ at 1 meter. At least a portion of an inner surface of the back wall may include a reflective surface. One or more of the first side wall, second side wall and back wall may include at least one removable panel. The chamber may be configured to receive a piece of equipment within the interior of the chamber. The disinfection system may further include a top wall attached to a top portion of the first side wall, second side wall and back wall. The disinfection system may further include a front wall to close an opening of the chamber. The front wall may include a window comprising a material that allows visibility into the chamber while substantially blocking energy emitted from the energy sources from exiting the chamber. At least a portion of an inner surface of the front wall may include at least one reflective unit or reflective surface. The front wall may be connected to the first side wall or second side wall by at least one hinge. The front wall may include first and second portions, wherein the first portion of the front wall is connected to the first side wall by at least one hinge, and the second portion of the front wall is connected to the second side wall by at least one hinge. The front wall may include a roll-up door. The front wall of the disinfection system may comprise a curtain configured to close an opening of the chamber. At least a portion of an inner surface of the curtain may include a reflective surface. The disinfection system may further include a drawstring and pulley configured to move the curtain between an open and closed configuration. The disinfection system may further include a bottom wall attached to a bottom portion of the first side wall, second side wall and back wall. A portion of the bottom wall may include a ramped surface. A portion of the bottom wall may decline toward the back wall. The bottom wall may include at least one stopper. The at least one stopper may be slidably disposed within at least one track disposed within the bottom wall. The at least one stopper may be attached to a handle. An inner surface of the bottom wall may include at least one reflective unit. The at least one reflective unit may be elevated above the inner surface of the bottom wall. The bottom wall may further include first and second treads, with an upper surface of each tread being substantially even with an upper surface of the elevated at least one reflective unit. The disinfection system may further include a ramp, wherein a first edge of the ramp is flush with the upper surface of the first and second treads, and a second edge of the ramp is flush with an outer surface of the bottom wall. Each of the plurality of rolling elements may be configured to move between a first position and a second position. The rolling elements may extend beyond the bottom portion of the chamber when in the first position, and may not extend beyond the bottom portion of the chamber when in the second position. Each of the rolling elements may include a piston assembly configured to move each rolling element between the first and second positions. The piston assembly may include a piston, a control rod and a housing of the rolling elements. A first end of the piston may be fluidly connected to a gas source, a second end of the piston may be attached to a first end of the control rod, and a second end of the control rod may be attached to the housing. Each rolling element may move from the second position to the first position by introducing gas from the gas source into the piston, and each rolling element may move from the first position to the second position by returning the introduced gas from the piston to the gas source or venting the introduced gas to atmosphere. The gas source may include a compressed gas source. The disinfection system may include a control panel on an outer surface of the chamber, such as the first side wall, second side wall, top wall, back wall or front wall. The control panel may be configured to electrically communicate with one or more sensors on or within the chamber. The one or more sensors may include a motion sensor configured to detect motion around the chamber. The one or more sensors may include a motion sensor configured to detect motion within the chamber. The one or more sensors may be configured to determine if the front wall is open. The one or more sensors may be configured to determine if a vertical plane parallel with the front wall is broken. The one or more sensors may include an electronic sensor configured to detect and/or differentiate pathogens on or within the chamber. The electronic sensor may be configured to determine the approximate quantity of pathogens on or within the chamber. The one or more sensors may include a UV light sensor configured to (i) output information that is representative of the intensity of UV light emitted within the chamber and/or (ii) detect UV light emitted from the chamber. The one or more sensors may include a camera to monitor and/or record the chamber during a disinfection procedure. The control panel may include an indicator of a status of the chamber. The status of the chamber may include a clock indicating the time remaining on a disinfection procedure. The control panel may be configured to electrically communicate with a reserve power source. The control panel may include a user interface, and the disinfection system may further comprise a central processing unit and non-transitory computer readable storage medium, with computer executable code embodied therein which, when executed by the central processing unit, causes the disinfection system to perform one or more administrative functions or operational functions based on user input and/or feedback from the one or more sensors. The one or more operational functions may include adjusting the intensity of the energy source from one or more of the reflective units.

In another aspect, the present disclosure relates to a disinfection system comprising a base, a first stack of reflective units rotatably attached to a top surface of the base and a first array of energy sources housed within the first stack of reflective units. The first stack of reflective units may be rotatably attached to the top surface of the base by a center shaft that extends from the top surface of the base through a center portion of the first stack of reflective units. The first stack of reflective units may include a first reflective unit, a second reflective unit, a third reflective unit and a fourth reflective unit. The units of the first stack may be arranged symmetrically about the center shaft. The first array of energy sources may include a first energy source, a second energy source, a third energy source and a fourth energy source. The disinfection system may further include a second stack of reflective units and a second array of energy sources housed within the second stack of reflective units. The second stack of reflective units may include a fifth reflective unit, a sixth reflective unit, a seventh reflective unit and an eighth reflective unit. The units of the second stack may be arranged symmetrically about the center shaft. The second array of energy sources may include a fifth energy source, a sixth energy source, a seventh energy source and an eighth energy source. The second stack of reflective units may be disposed on top of or alongside the first stack of reflective units. Each of the first, second, third and fourth reflective units may rotate around their respective first, second, third or fourth energy sources within the first stack of reflective units. Each of the first, second, third and fourth reflective units may rotate with their respective first, second, third or fourth energy sources within the first stack of reflective units. The first, second, third and fourth reflective units may be rotatable such that when rotated a respective reflective surface of each reflective unit faces away from the center shaft or toward the center shaft. Each of the fifth, sixth, seventh and eighth reflective units may rotate around their respective fifth, sixth, seventh and eighth energy sources within the second stack of reflective units. Each of the fifth, sixth, seventh and eighth reflective units may rotate with their respective fifth, sixth, seventh and eighth energy sources within the second stack of reflective units. The fifth, sixth, seventh and eighth reflective units may be rotatable such that when rotated a respective reflective surface of each reflective unit faces away from the center shaft or toward the center shaft. The disinfection system may further include a pivot point driver extending through an inner portion of the center shaft, wherein respective first, second, third and fourth arms may extend from a top portion of the pivot point driver to a pivot point on each of the first, second, third and fourth reflective units. The same or another pivot point driver may have additional arms that extend from the pivot point driver to a pivot point on each of the fifth, sixth, seventh and eighth reflective units. Each of the reflective units of the first and second stacks may define a substantially concave shape. The first and second arrays of energy sources may include an ultraviolet light source. Each ultraviolet light source may be configured to emit ultraviolet energy at an intensity of at least 100 µW/cm$^2$ at 1 meter. The disinfection system may further include a plurality of rolling elements attached to a bottom surface of the base. The base may be a robotic base configured to be programmed with disinfecting parameters and contours or waypoints of a space, whereby the robotic base may automatically move about and disinfect the space according to the parameters and one or both of the contours and waypoints of the space.

In yet another aspect, the present disclosure relates to a disinfection system comprising a robotic chamber comprising a first side wall, a second side wall and a back wall. A surface of each of the first side wall, second side wall and back wall may include at least one reflective unit. At least one energy source may be housed within each reflective unit. A plurality of rolling elements may be disposed along a bottom surface of the chamber. The rolling elements may be configured to move between a first position extending beyond the bottom surface of the chamber, and a second position where the rolling elements do not extend beyond the bottom surface of the chamber. The robotic base may include a user interface, central processing unit and non-transitory computer readable storage medium, with computer executable code embodied therein which, when executed by the central processing unit, causes the robotic base to move between points of disinfection, control one or more disinfection operations of the system, monitor one or more sensors of the system or adjust the intensity of the energy source of one or more of the reflective units, based on input from the user interface or based on feedback received from the one or more sensors. The disinfection system may further include a front wall, wherein a surface of the front wall may include at least one reflective unit or reflective surface. The disinfection system my further include a top wall and a bottom wall, wherein a surface of each of the top wall and bottom wall may include at least one reflective unit. The surface of each of the first side wall, second side wall, front wall, back wall, top wall and bottom wall, including the at least one reflective unit or reflective surface, may face into the interior of the chamber. The surface of each of the first side wall, second side wall, front wall and back wall including the at least one reflective unit or reflective surface, may face outward from the chamber.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 3A-3B provide perspective views of a disinfection system, according to one embodiment of the present disclosure.

DETAILED DESCRIPTION

Figure 1A:
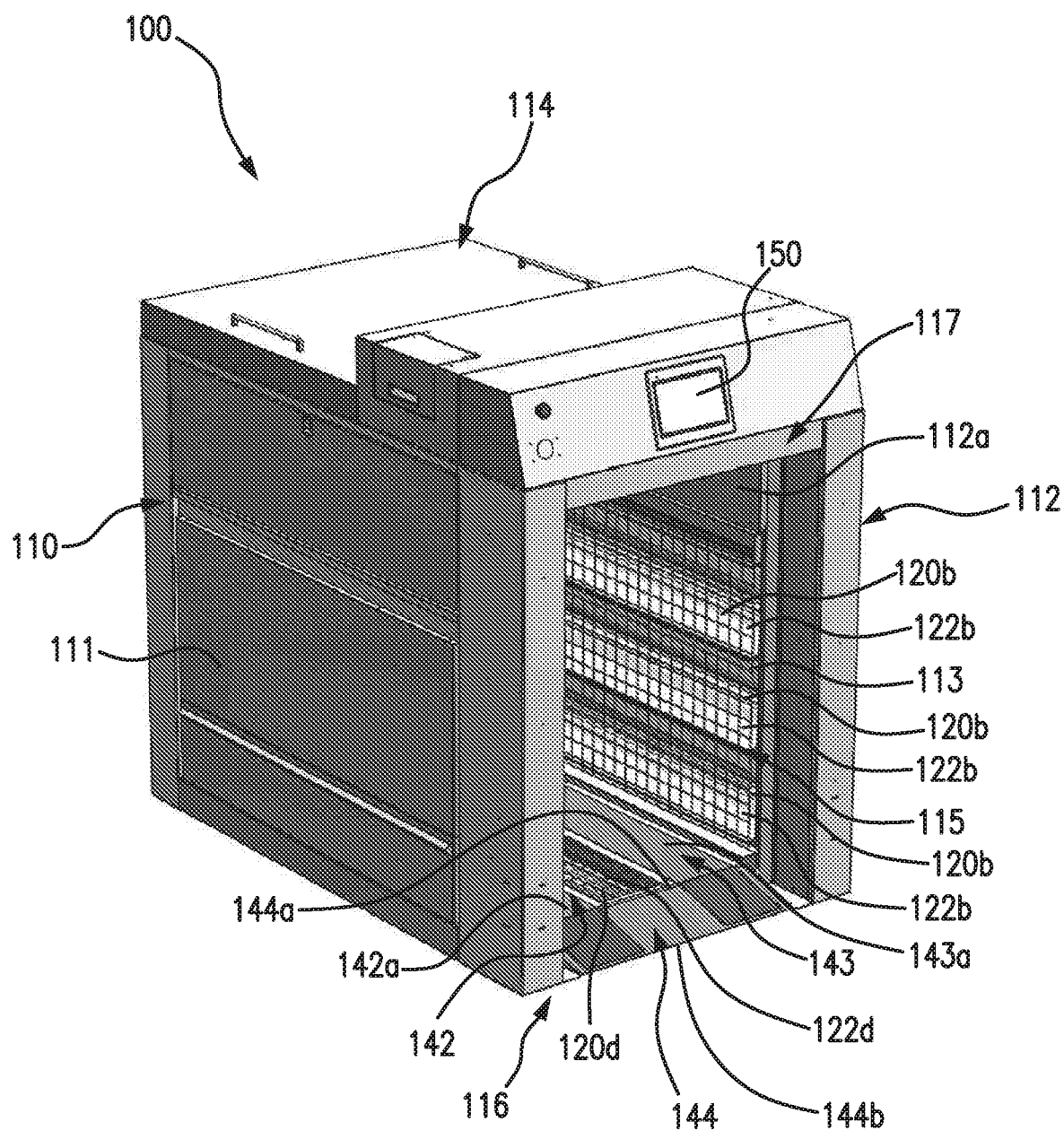
FIGS. 1A-1I provide perspective views of a disinfection system, according to one embodiment of the present disclosure.
Figure 1B:
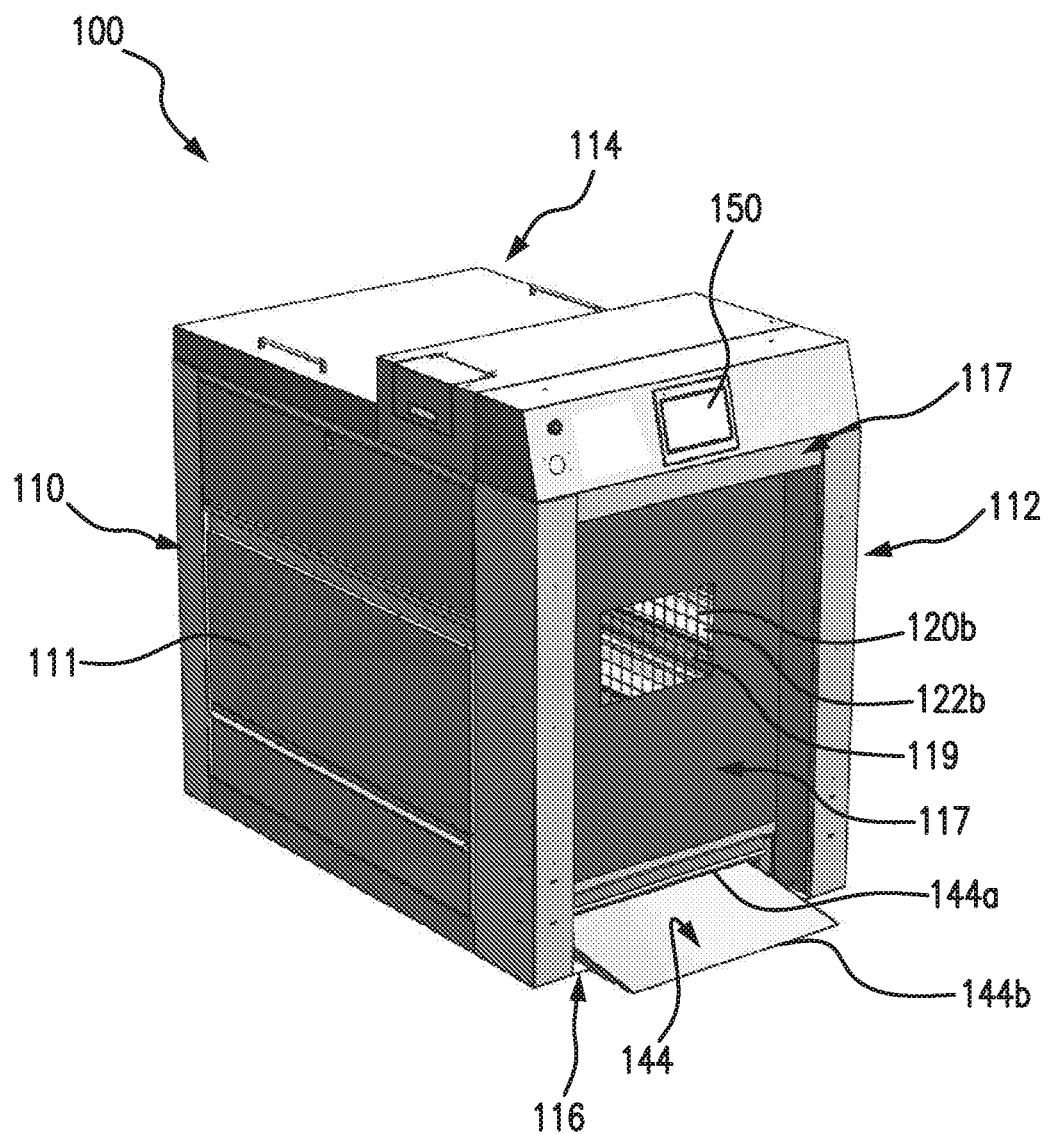

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to systems and methods for disinfecting medical equipment (e.g., gurneys, wheelchairs, IV poles, dialysis machines, etc.) or medical enclosures (e.g., hospital rooms, surgery suites, diagnostic laboratories, etc.), it should be appreciated that such systems and methods may be used to disinfect a variety of items used or contacted by the public (e.g., shopping carts, shopping baskets, strollers, railings, door knobs, etc.) and a variety of enclosures (e.g., kitchens, public or private bathrooms, cafeterias, airplanes, buses, etc.).

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "equipment," refers to any portable or moveable item contacted, carried and/or moved outside the strict control and/or view of the items' owner(s), and may include, for example, all of the examples provided above, among other examples.

As used herein, the term "reflective unit" refers to a collection of reflective sections. Such units, when taken in various grouping, together reflect a certain percentage of light at a given range of frequency of light, e.g., at least 60% of light having a frequency between 100 nm to 290 nm.

As used herein, the term "disinfect" and "sanitize," or grammatical equivalents thereof, indicate the expectation that pathogen (e.g., bacteria, viruses, etc.) count will be substantially reduced or eliminated on irradiated equipment. The dose of UV light required to kill pathogens corresponds to the UV light intensity as a function of time. Dose response levels are unique to each microorganism. Additionally, different wavelengths of UV light have different inactivation rates depending on the microorganism. However, for most microorganisms the peak inactivation wavelength is, e.g., at or about 260 nanometers (nm).

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

In various embodiments, the present disclosure relates to systems and methods which emit energy, including, e.g., UV light, with the combined benefits of intensity, proximity and line of sight to disinfect equipment and/or spaces. Referring to FIGS. 1A-1I, in one embodiment, a disinfection system 100 of the present disclosure may include a chamber 115 comprising a first side wall 110 (e.g., left wall), a second side wall 112 (e.g., right wall), a bottom wall 116 (e.g., floor), a front wall 117 (e.g., front door), a back wall 118 (e.g., back door) and a top wall 114 (e.g., ceiling). An inner surface 110a of the first side wall 110 may include at least one reflective unit 120a, an inner surface 112a of the second side wall 112 may include at least one reflective unit 120b, an inner surface 114a of the top wall 114 may include at least one reflective unit 120c and an inner surface 116a of the bottom wall 116 may include at least one reflective unit 120d. Similarly, at least a portion of an inner surface 117a of the front wall 117 may include a reflective surface and at least a portion of an inner surface 118a of the back wall 118 may include a reflective surface. At least one energy source 122a-d may be removably or permanently disposed within (e.g., partially surrounded by) each of the at least one reflective units 120a-d such that energy emitted from each energy source is directed into the chamber and/or a piece of equipment disposed therein. For example, an energy source 122a may be disposed within each reflective unit 120a of the first side wall 110, an energy source 122b may be disposed within each reflective unit 120b of the second side wall 112, an energy source 122c may be disposed within each reflective unit 120c of the top wall 114 and an energy source 122d may be disposed within each reflective unit 120d of the bottom wall 116. A plurality of rolling elements 132a-c (e.g., wheels, casters, sleds, etc.) may be disposed along an outer surface 116b of the bottom wall 116 of the chamber 115. For example, a first rolling element 132a may be disposed below a front-left corner of the chamber 115, a second rolling element 132b may be disposed below a front-right corner of the chamber 115 and a third rolling element may be disposed below the back wall 118 of the chamber 115.

In various embodiments, each of the reflective units 120a-d may be oriented or positioned on the respective inner surface 110a, 112a, 114a 116a of the first side wall 110, second side wall 112, top wall 114 and bottom wall 116 such that a reflective surface of each reflective unit faces (e.g., is directed towards) the chamber 115. In addition, each reflective unit 120a-d may be independently adjustable such that the direction or angle of the reflective unit may be adjusted, e.g., manually or automatically. Each reflective unit 120a-d may define or include a substantially concave shape such that energy emitted from each of the respective energy sources 112a-d is directed or focused into the chamber 115. By way of non-limiting example, each reflective unit 120a-d may include a back section, and at least three reflective sections, each of which may be disposed off normal with respect to the back section. This configuration of reflective sections may allow energy emitted from the energy sources to be directed in every direction into the chamber 115, rather than only up and down or left and right. In this manner, disinfecting energy may be directed onto multiple surfaces of a piece of equipment housed within the chamber with the proper intensity, proximity and line of sight to provide disinfecting consistency and optimal coverage with energy, requiring fewer energy sources and/or shorter exposure to the energy source (e.g., increased efficiency). In various embodiments, each of the reflective units 120a-d (including the reflective surfaces) may comprise one or more commercially suitable materials, including, for example, mirrors, powder-coated and other metal sheets, and Pebbletone™ and Hammertone™ finishes.

In various embodiments, each of the energy sources 122a-d may be configured to emit ultraviolet (UV) light. For example, each energy source may include mercury vapor bulbs or tubes, xenon gas bulbs or tubes, light emitting diodes (LED), light emitting nanoparticles, or any other energy source configured to emit ultraviolet (UV) light at a wavelength of approximately 320-400 nm (e.g., UV-A), approximately 290-320 nm (e.g., UV-B) and/or approximately 200-280 nm (e.g., UV-C). Each energy source 122a-d may include dual UV emitting bulbs, although the number of bulbs may be varied. Although the UV emitting bulbs are depicted as elongate bulbs, other suitable UV emitting sources may include, by way of non-limiting example, a 36 Watt bulb that emits UV light at a wavelength of approximately 254 nm. Although any of the UV-A, UV-B, or UV-C wavelengths of energy may provide sufficient disinfection of equipment within the chamber, in one embodiment an energy source configured to emit at least 30 watts of UV energy, at least 75% of which is UV-C energy, may provide an optimal disinfection intensity. In addition, or alternatively, the UV energy emitting source may include a light emitting diode (LED) and/or light emitting nanoparticles deposited or grown on a flexible metallic surface, as such components and processes for producing such components are known in the art.

In one embodiment, the reflective units 120a, 120b, 120d, and respective energy sources 122a, 122b, 122d disposed therein, may be arranged in substantially parallel rows along the respective inner surfaces 110a, 112a, 116a, of the first side wall 110, second side wall 112 and bottom wall 116 of the chamber 115, and the reflective units 120c and respective energy sources 122c disposed therein, may be arranged in substantially parallel rows along the inner surface 114a of the top wall 114 perpendicular to the reflective units 120a, 120b, 120d. However, the present disclosure is in no way limited to this arrangement of reflective units and/or energy sources, and may include reflective units and energy sources disposed in any suitable location, orientation, configuration, size and/or number such that equipment within the chamber 115 is exposed to energy with an intensity, proximity (e.g., at least 100 µW/cm² at 1 meter) and line of sight to facilitate efficient disinfection.

In one embodiment, the front wall 117 may be electronically or manually operated and may be sized and dimensioned to effectively cover an opening to the chamber 115. The front wall 117 may further include a window 119 to allow a user to monitor equipment being disinfected within the chamber and/or ensure proper functioning of each energy source 122a-d throughout a disinfection procedure. The window 119 may include a suitable UV reflecting, blocking or absorbing material (e.g., UV protective coating, layer, or polarized material) to block, filter or otherwise prevent UV energy from exiting the chamber, thereby negating the associated risks from exposure to UV energy. In one embodiment, the front wall 117 may include a flexible sheet of material (e.g., metal, cloth, fabric, plastic, etc.) configured to move from a closed configuration in which the flexible sheet of material covers an opening to the chamber, and an open configuration in which the flexible sheet of material is rolled around a cylinder disposed within a front portion of the top wall 114. Alternatively, the front wall 117 may be attached to the chamber 115 by at least one hinge (not shown), or other suitable pivoting connecting element, such that the front wall may pivot between an open and closed configuration. Alternatively, the front wall 117 may include a split (e.g., French door) configuration, in which a first portion of the front wall 117 is connected to the first side wall 110 by at least one hinge (not shown) and a second portion of the front wall 117 is connected to the second side wall 110 by at least one hinge (not shown), such that the first and second portions may individually pivot between an open and closed configuration. At least a portion of an inner surface of the front wall 117 may include a reflective surface to redirect energy emitted from the energy sources 122a-d into the chamber 115. Additionally, or alternatively, at least a portion of an inner surface of the front wall 117B may include at least one reflective unit with at least one energy source housed therein. Regardless of the specific configuration, the front wall 117 may be configured to prevent children, animals and others from entering the chamber while the energy sources are activated. With the front wall 117 open, one or more pieces of equipment may be introduced into the chamber 115. All commercially viable sizes are contemplated for the chamber 115. By way of non-limiting example, a chamber dimensioned to receive a standard sized wheel chair may include an inner length of approximately 48 inches, an inner height of approximately 48 inches and an inner width of approximately 36 inches. In various embodiments, the size and dimensions of the opening and interior portion of the chamber may vary depending on the equipment to be disinfected, such as hospital gurneys, medical equipment consoles, IV poles, etc.

In one embodiment, the back wall 118 may provide an alternate access point or opening to the interior of the chamber 115. For example, a user may open the back wall 118 to repair or inspect the chamber, help introduce equipment into or remove equipment from the chamber 115 and/or remove dislodged components of the equipment that may be preventing the equipment from being introduced into or removed from the chamber 115.

In various embodiments, rolling elements may be employed with a chamber. For example, in one embodiment, rolling elements 132a-c may be configured to move between a first position in which the rolling elements extend beyond (e.g., below) the outer surface 116b of the bottom wall 116 (e.g., FIGS. 1E-1G), and a second position in which the rolling elements do not extend beyond the outer surface 116b of the bottom wall 116 (e.g., FIGS. 1A-1D and 1H-1I). With the rolling elements 132a-c in the first position (e.g., deployed or exposed), the chamber 115 may be manually or robotically moved (e.g., rolled). With the rolling elements 132a-c in the second position (e.g., retracted into a recess formed within the bottom wall 116), the bottom surface 116d of the bottom wall 116 may be placed in contact with the floor underneath the chamber 115, thereby minimizing movement of the disinfection system 100 during storage and/or use. In various embodiments, the three-rolling element configuration depicted in FIGS. 1A-1I may allow the disinfection system 100 to turn or spin within a tight radius for maneuvering, e.g., through the hallways and/or rooms of a hospital. However, the present disclosure is in no way limited to the configuration of rolling elements depicted herein, and may include any number of rolling elements arranged in various locations along the bottom surface 116b of the bottom wall 116.

In one embodiment, a rolling element of the present disclosure may be attached to a piston 133 configured to move the rolling element between the first and second positions. For example, a first end 133a of the piston 133 may be fluidly connected to a compressed gas source 134 by a length of hydraulic tubing 137, and a second end 133b of the piston 133 may be attached to a first end 135a of a control rod 135, and a second end 135b of the control rod 135 may be attached to a housing of the rolling element. Each rolling element 132a-c may simultaneously move from the second position to the first position by introducing (e.g., flowing) gas from the compressed gas source 134 into the piston 133 such that the control rod 135 is forced downward (e.g., away from the outer surface 116b of the bottom wall 116, thereby simultaneously placing each rolling element 132a-c in contact with the floor to elevate or raise the disinfection system 100 such that the outer surface 116b of the bottom wall 116 no longer contacts the floor. Similarly, each rolling element 132a-c may simultaneously move from the first position to the second position by returning (e.g., flowing) introduced gas from the piston 133 to the compressed gas source 134 such that the control rod 135 is drawn upward (e.g., toward the outer surface 116b of the bottom wall 116, thereby retracting each rolling element 132a-c into a recess formed within the bottom wall 116 to lower the disinfection system 100 such that the outer surface 116b of the bottom wall 116 contacts the floor. Alternatively, each rolling element 132a-c may move from the first to second position by venting introduced gas from within the piston 133 into the atmosphere. The rolling elements may also be configured to be controlled, and raised and lowered, independent of each other, as desired. The gas source may come from a house source, such as gas supplied by a hospital to the room, or may be a dedicated source housed on the chamber, for example, the compressed gas source as shown in FIG. 1D, which may be periodically replenished or replaced.

Figure 1C:
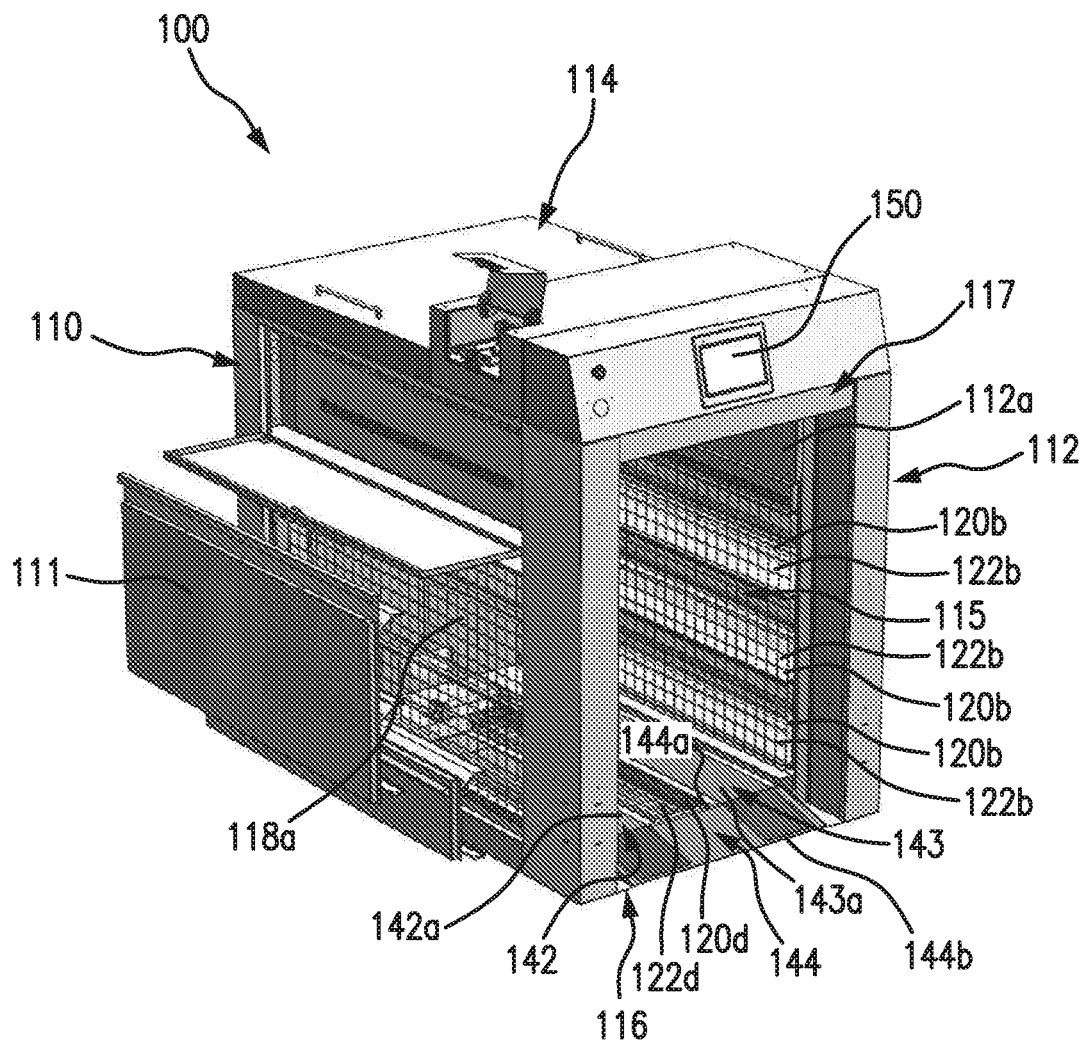
Figure 1D:
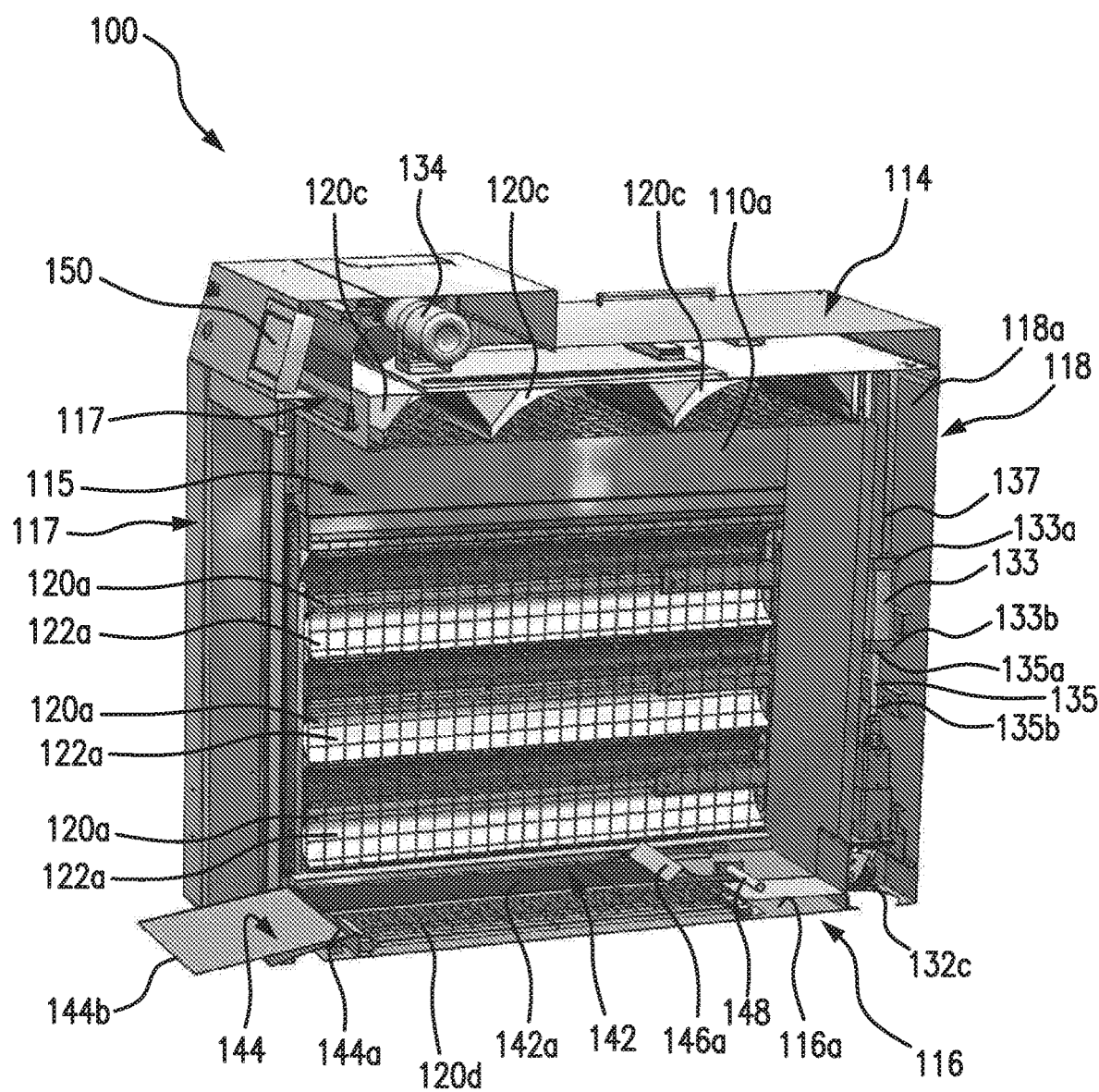
Figure 1E:
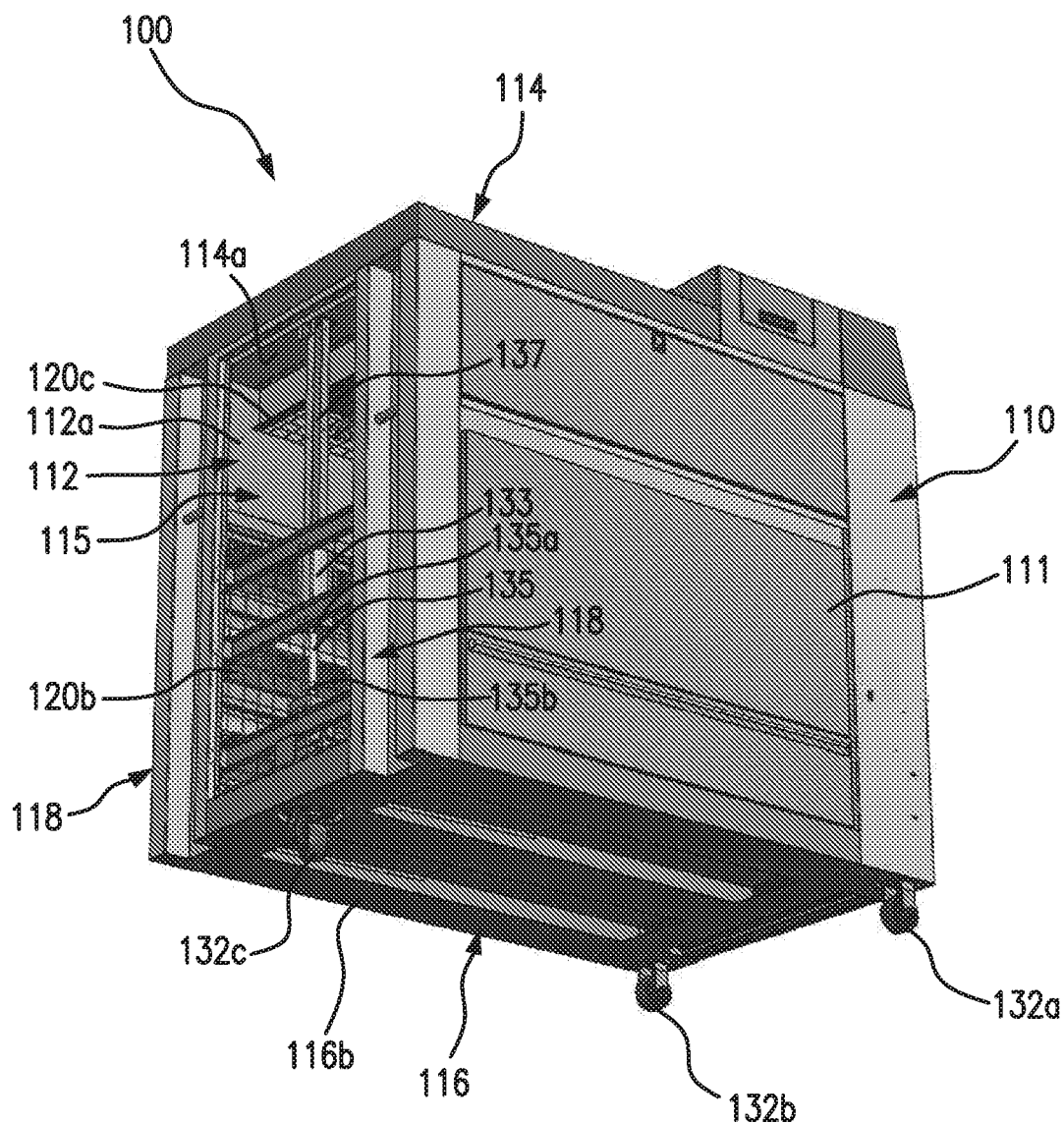
Figure 1F:
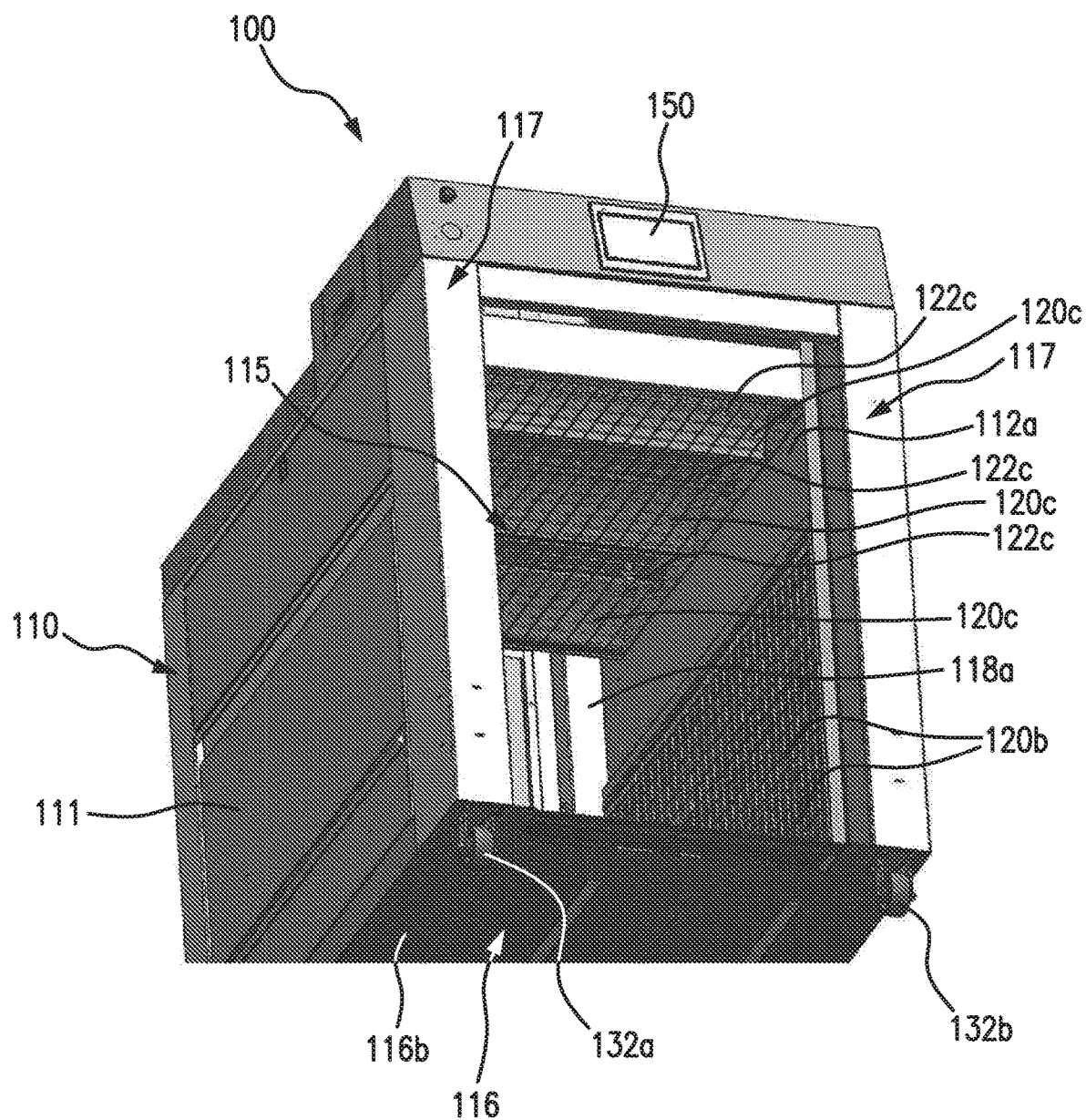
Figure 1G:
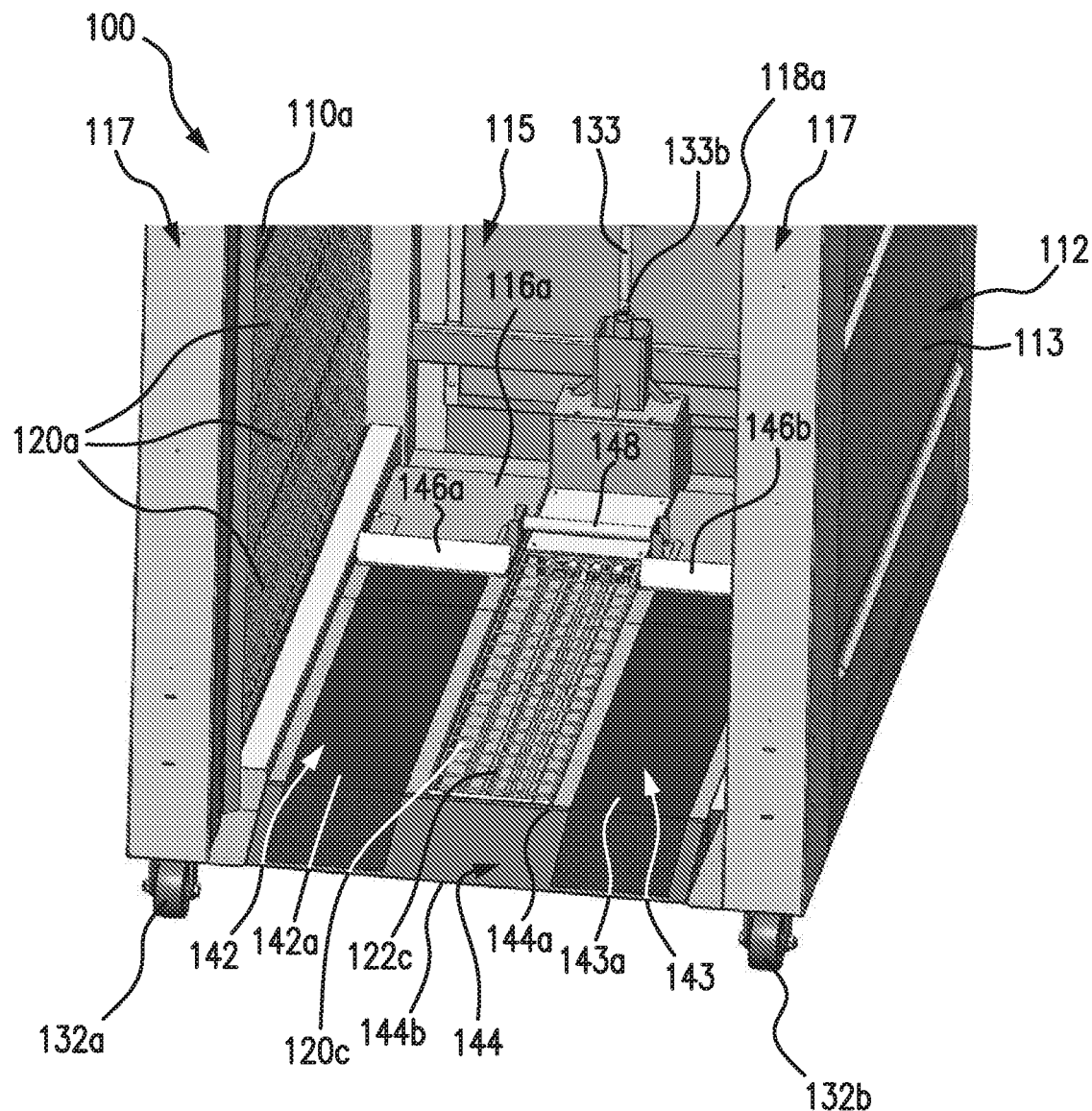
Figure 1H:
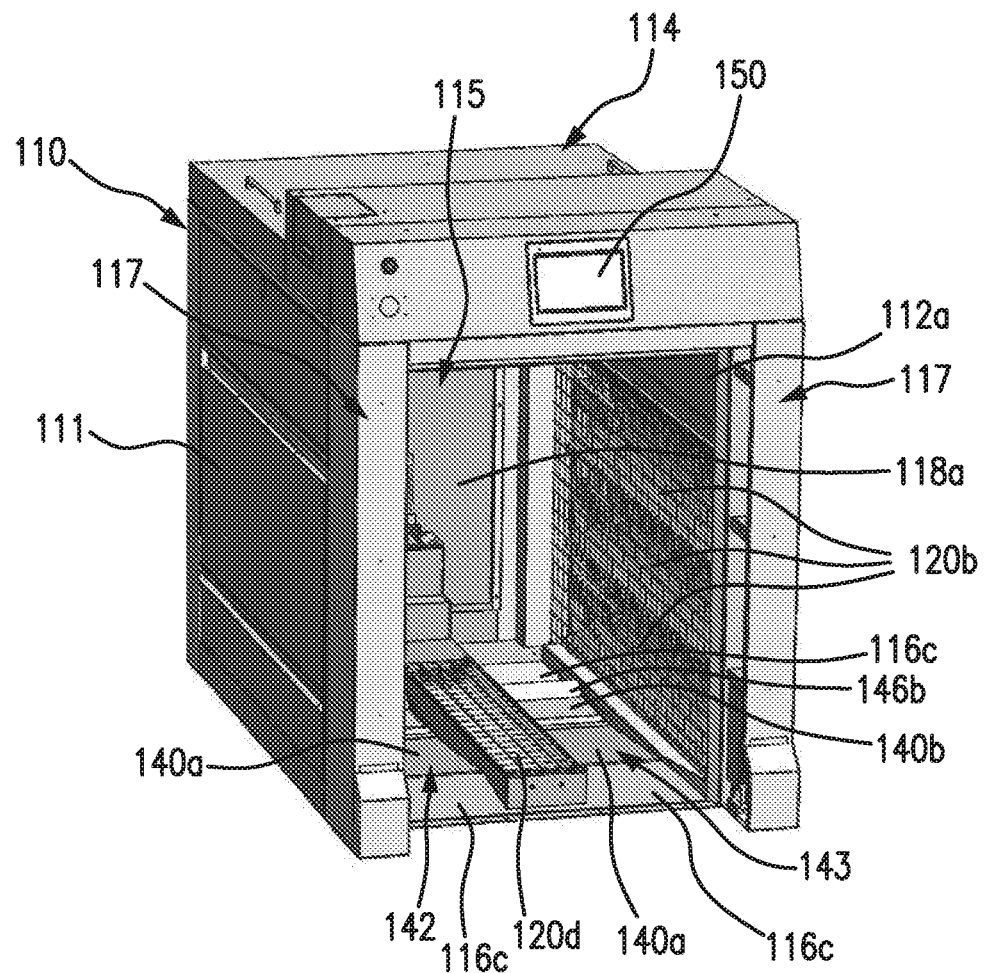
Figure 1I:
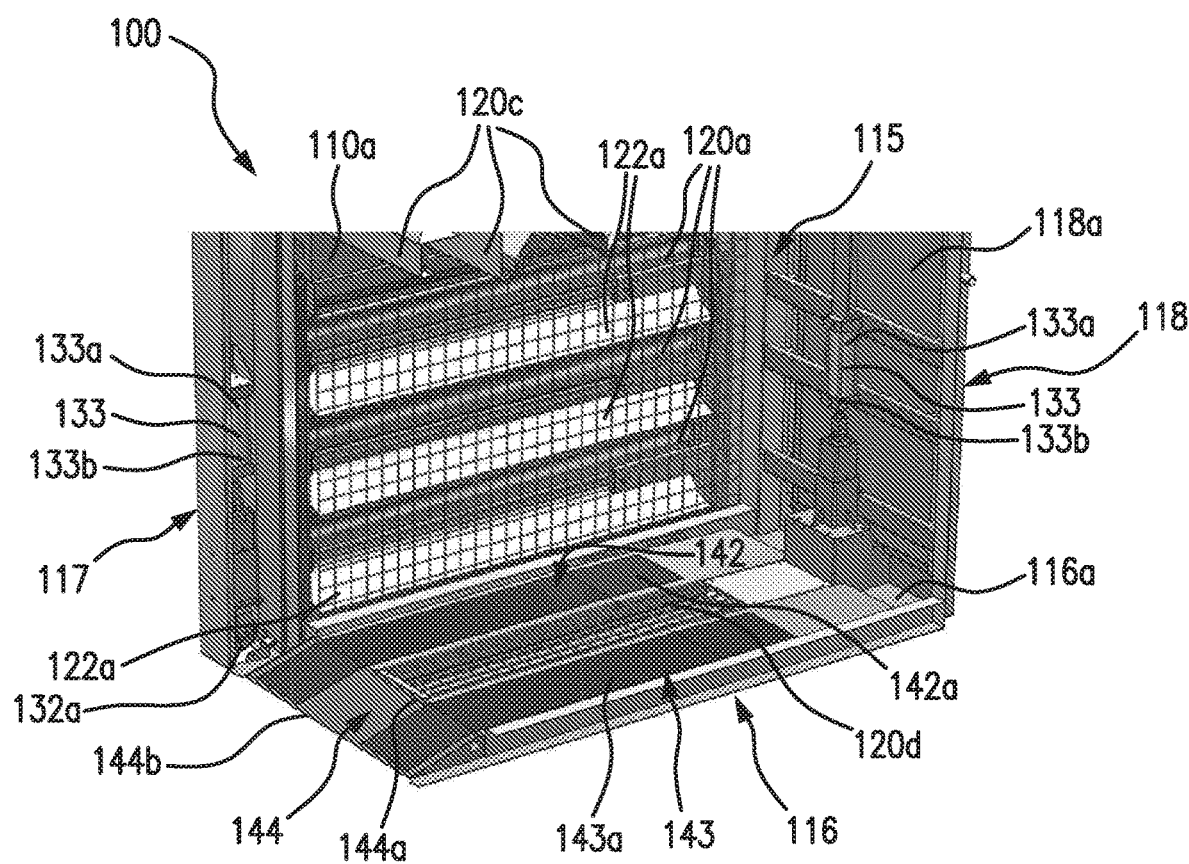

Referring to FIG. 1H, in one embodiment, a portion of the bottom wall 116 may include a ramped surface 116c that declines at an angle toward the front wall 117 such that equipment may be rolled into or out of the chamber 115. The ramped surface 116 may include a variety of different lengths and/or pitches, e.g., a long ramp with a shallow gradient to accommodate the rolling of heavy equipment. Another portion of the bottom wall 116 may include a ramped surface 140a that declines at an angle toward the back wall 118, and a ramped surface 140b that declines toward the front wall 117 such the equipment (e.g., equipment on wheels, etc.) does not roll out of the chamber 115 or contact the back wall. This may be beneficial, for example, to retain equipment within the chamber until the front wall 117 is closed, or to prevent the equipment from rolling out of the chamber as the front wall 117 is opened following a disinfection procedure.

In various embodiments, the reflective unit 120c and energy source 122c may be elevated above the inner surface 116a of the bottom wall 116. This may present a problem when introducing certain equipment into the chamber 115, including, e.g., electric wheelchairs that do include the requisite clearance to pass over the reflective unit 120c. Accordingly, in one embodiment, a chamber 115 of the present disclosure may include first and second treads 142, 143 disposed on opposite sides of the reflective unit 120c and energy source 122c. The first and second treads 142, 143 may include a sufficient thickness or height such that an upper surface 142a, 143a of each tread may be even or flush with an upper edge of the reflective unit 120c. In one embodiment, the chamber 115 may include a ramp 144 with comprising a first edge 144a that is flush or even with the upper surfaces 142a, 143a of the first and second treads 142, 143 and a second edge 144b that is flush or even with an outer surface 116b of the bottom wall 116. The ramp 144 may include a variety of different lengths and/or pitches, e.g., a long ramp with a shallow gradient to accommodate the rolling of heavy equipment. In addition, ramp 144 may include a pivot connection to allow the ramp to be rotated into the chamber 115 during storage, movement and/or activation of the disinfection system 100. In one embodiment, a first stopper 146a may be attached to the first tread 142 and a second stopper 146b may be attached to the second tread 143. The first and second stoppers 146a, 146b may be configured to maintain proper position of a piece of equipment within the chamber 115 and/or prevent the equipment from advancing too far into the chamber 115. For example, the first and second stoppers 146a, 146b may provide a contact point for equipment with wheels, such that the equipment is prevented from contacting the back wall 118, thereby limiting the likelihood of damage to the equipment and/or back wall 118 while also maintaining the equipment in a proper position for optimal disinfection. In one embodiment, the first and second stoppers 146a, 146b may be disposed within a groove or track formed within each of the first and second treads 142, 143 such that a position of the first and second stopper 146a, 146b along the respective first and second treads 142, 143 may be adjusted to accommodate equipment of various sizes and/or multiple pieces of equipment. In one embodiment, the first and second stoppers 146a, 146b may be attached by a handle 148 such that the position of the first and second stoppers 146a, 146b may be adjusted simultaneously. In various embodiments, the first and second stoppers 146a, 146b may be moved or repositioned along the respective first and second treads 142, 143 either manually or using automated controls. In addition, or alternatively, the bottom wall 116 and/or first and second treads 142, 143 may include a conveyor system configured to automatically feed equipment into and out of the chamber 115. For example, a conveyor system may include a conveyor, belts, tracks and/or a combination thereof. Alternatively, the equipment may be manually or automatically pushed into the chamber using, e.g., a cart mover.

In one embodiment, the first side wall 110 may include at least one removable panel 111, and the second side wall 112 wall may include at least one removable panel 113 to allow the reflective units 120a, 120b and energy sources 122a, 112b to be inspected, repaired or replaced (FIG. 1C). Other of the walls of a chamber may include at least one removable panel to allow reflective units attached to panel to be inspected, repaired or replaced.

Referring to FIGS. 2A-2F, in one embodiment, a disinfection system 200 of the present disclosure may include a chamber 215 comprising a first side wall 210 (e.g., left wall), a second side wall 212 (e.g., right wall) and a back wall 214 (e.g., rear wall). The first and second side walls 210, 212 may extend substantially perpendicular to the back wall 214 to define a chamber 215 with a U-shaped cross-section. The present disclosure is not limited to a chamber with a U-shaped cross-section (FIG. 2D), but may include a variety of shapes and/or dimensions. For example, the first and second side walls 210, 212 may extend from the back wall at an angle greater than 90 degrees (e.g., 100 degrees or more, 110 degrees or more, 120 degrees or more, etc.), to define a chamber 215 with an opening that is larger than a width of the back wall 214 (not shown). An inner surface 210a of the first side wall 210 may include at least one reflective unit 220a, an inner surface 212a of the second side wall 212 may include at least one reflective unit 220b and an inner surface 214a of the back wall 214 may include at least one reflective unit 220c. At least one energy source 222a-c may be removably or permanently disposed within (e.g., partially surrounded by) each of the at least one reflective units 220a-c such that energy emitted from each energy source is redirected into the disinfection chamber and/or a piece of equipment disposed therein. For example, an energy source 222a may be disposed within each reflective unit 220a of the first side wall 210, an energy source 222b may be disposed within each reflective unit 220b of the second side wall 212, an energy source 222c may be disposed within each reflective unit 220c of the back wall 214. In one embodiment, each of the first side wall 110, second side wall 212 and back wall 214 may include at least one removable panel (not shown) to allow the respective reflective units 220a, 220b, 220c and energy sources 222a, 222b, 22c to be inspected, repaired or replaced. A plurality of rolling elements 232a-d (e.g., wheels, casters, sleds, etc.) may be disposed along a bottom portion of the first side wall 210, second side wall 212 and/or back side wall 214. For example, a first rolling element 232a may be disposed below a front portion of the first side wall 210, a second rolling element 232b may be disposed below a junction of the first side wall 210 and back wall 214, a third rolling element 232c may be disposed below a junction of the second side wall 212 and back wall 214 and a fourth rolling element 232d may be disposed below a front portion of the second side wall 212. As another example, three-walled chambers may be fitted with three rolling elements such as described above to allow for steering and increased maneuverability in tight spaces.

In various embodiments, each of the reflective units 220a-c may be oriented or positioned on the respective inner surface 210a, 212a, 214a of the first side wall 210, second side wall 212 and back wall 214 such that a reflective surface of each reflective unit faces (e.g., is directed towards) the chamber 215. In addition, each reflective unit 220a-c may be independently adjustable such that the direction or angle of the reflective unit may be adjusted, e.g., manually or automatically. Each reflective unit 220a-c may define or include a substantially concave shape such that energy emitted from each of the respective energy sources 222a-c is directed or focused into the chamber 215. By way of non-limiting example, each reflective unit 220a-c may include a back section, and at least three reflective sections, each of which may be disposed off normal with respect to the back section. This configuration of reflective sections may allow energy emitted from the energy sources to be directed in every direction into the chamber 215 rather than only up and down or left and right. In this manner, disinfecting energy may be directed onto multiple surfaces of a piece of equipment housed within the chamber with the proper intensity, proximity and line of sight to provide disinfecting consistency, requiring fewer energy sources and/or shorter exposure to the energy source (e.g., increased efficiency). In various embodiments, each of the reflective units 220a-c (including the reflective surfaces) may comprise one or more commercially suitable materials, including, for example, mirrors, powder-coated and other metal sheets, and Pebbletone™ and Hammertone™ finishes.

In various embodiments, each of the energy sources 222a-c may be configured to emit ultraviolet (UV) light. For example, each energy source may include mercury vapor bulbs or tubes, xenon gas bulbs or tubes, light emitting diodes (LED), light emitting nanoparticles, or any other energy source configured to emit ultraviolet (UV) light at a wavelength of approximately 320-400 nm (e.g., UV-A), approximately 290-320 nm (e.g., UV-B) and/or approximately 200-280 nm (e.g., UV-C). Each energy source 222a-c may include dual UV emitting bulbs, although the number of bulbs may be varied. Although the UV emitting bulbs are depicted as elongate bulbs, other suitable UV emitting sources may include, by way of non-limiting example, a 36 Watt bulb that emits UV light at a wavelength of approximately 254 nm. Although any of the UV-A, UV-B, or UV-C wavelengths of energy may provide sufficient disinfection of equipment within the chamber, in one embodiment an energy source configured to emit at least 30 watts of UV energy, at least 75% of which is UV-C energy, may provide an optimal disinfection intensity. In addition, or alternatively, the UV energy emitting source may include a light emitting diode (LED) and/or light emitting nanoparticles deposited or grown on a flexible metallic surface (FIG. 2C), as such components and processes for producing such components are known in the art.

In one embodiment, the reflective units 220a, 220b, 220c, and respective energy sources 222a, 222b, 222c disposed therein, may be arranged in substantially parallel rows along the respective inner surfaces 210a, 212a, 214a, of the first side wall 210, second side wall 212 and back wall 214 of the chamber 215. However, the present disclosure is in no way limited to this arrangement of reflective units and/or energy sources, and may include reflective units and energy sources disposed in any suitable location, orientation, configuration, size and/or number such that equipment within the chamber 215 is exposed to energy with adequate intensity, proximity (e.g., at least 100 µW/cm² at 1 meter) and line of sight to facilitate efficient disinfection.

In one embodiment, the chamber 215 may further include a curtain 216 as a front wall configured to move between an open configuration and a closed configuration (FIG. 2E) to seal or close an opening of the chamber 215. For example, the chamber 215 may include a pully 218 and drawstring 217 configured to manually or automatically move the curtain 216 between the open and closed configurations. The curtain 216 may include a flexible sheet of material (e.g., metal, cloth, fabric, plastic, etc.) sized and dimensioned to effectively cover the opening to the chamber 215. The curtain 216 may also include a sufficient length to contact the floor when in the closed configuration to prevent energy emitted from the energy sources 222a-c from exiting the chamber 215 during a disinfection procedure. At least a portion of an inner surface 216a of the curtain 216 may include a reflective surface to redirect energy emitted from the energy sources 222a-c into the chamber 215.

In one embodiment, the chamber 215 may further include a front wall 219 (e.g., door) configured to manually or automatically move between an open configuration and a closed configuration to seal or close an opening of the chamber 215. For example, the front wall 219 may be attached to the chamber 215 by at least one hinge (not shown), or other suitable pivoting connection element, such that the front wall may pivot between an open and closed configuration (FIG. 3A). Alternatively, the front wall 219 may include a first portion 219b connected to the first side wall 210 by at least one hinge (not shown) and a second portion 219c connected to the second side wall 210 by at least one hinge (not shown), such that the first and second portions 219b, 219c may individually pivot between an open and closed configuration (FIG. 3B). At least a portion of an inner surface 219a of the front wall 219 may include a reflective surface to redirect energy emitted from the energy sources 222a-c into the chamber 215. Additionally, or alternatively, at least a portion of an inner surface 219a of the front wall 219 may include at least one reflective unit with at least one energy source housed therein. The front wall 219 may further include a window (not shown) to allow a user to monitor equipment being disinfected within the chamber and/or ensure proper functioning of each energy source 222a-c throughout a disinfection procedure. The window may include a suitable UV reflecting, blocking or absorbing material (e.g., UV protective coating, layer, or polarized material) to block, filter or otherwise prevent UV energy from exiting the chamber, thereby negating the associated risks from exposure to UV energy. Regardless of the specific configuration, the front wall 219 may be configured to prevent children, animals and others from entering the chamber while the energy sources are activated.

In one embodiment, the chamber 215 may further include a top wall (e.g., ceiling, not shown) attached to a top portion of the first side wall 210, second side wall 212 and back wall 214. At least a portion of an inner surface of the top wall may include a reflective surface to redirect energy emitted from the energy sources 222a-c into the chamber 215. Alternatively, an inner surface of the top wall may include at least one reflective unit and least one energy source removably or permanently disposed within therein (as discussed above) such that energy emitted from each energy source is redirected into the chamber 215 and/or a piece of equipment disposed therein.

Figure 2A:
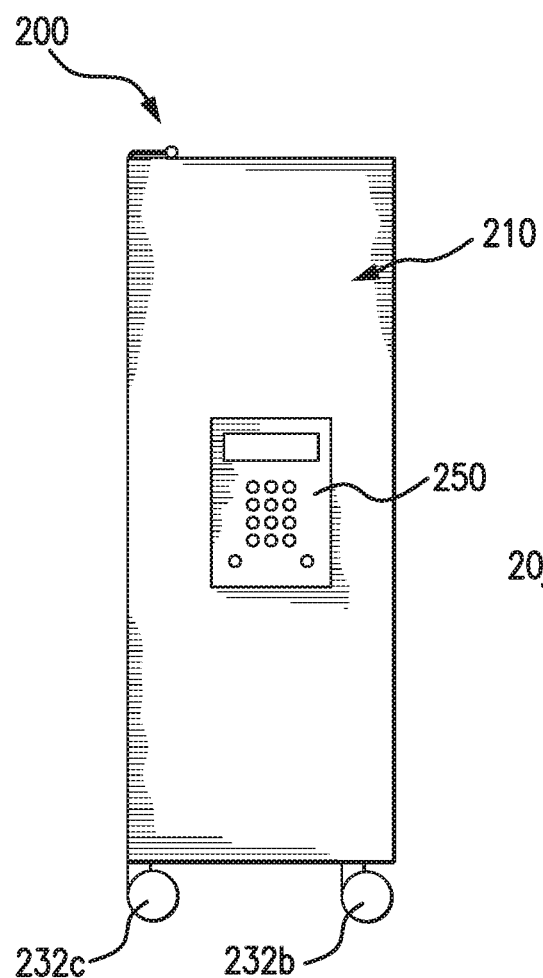
FIGS. 2A-2F provide perspective views of a disinfection system, according to one embodiment of the present disclosure.
Figure 2B:
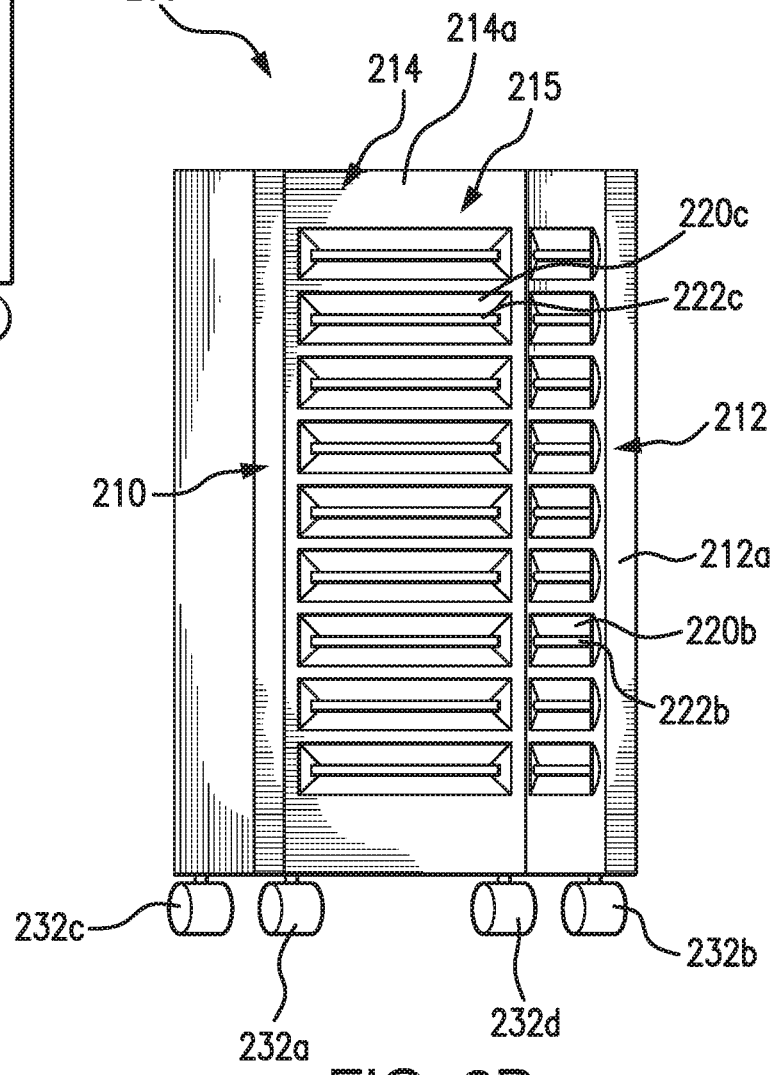
Figure 2C:
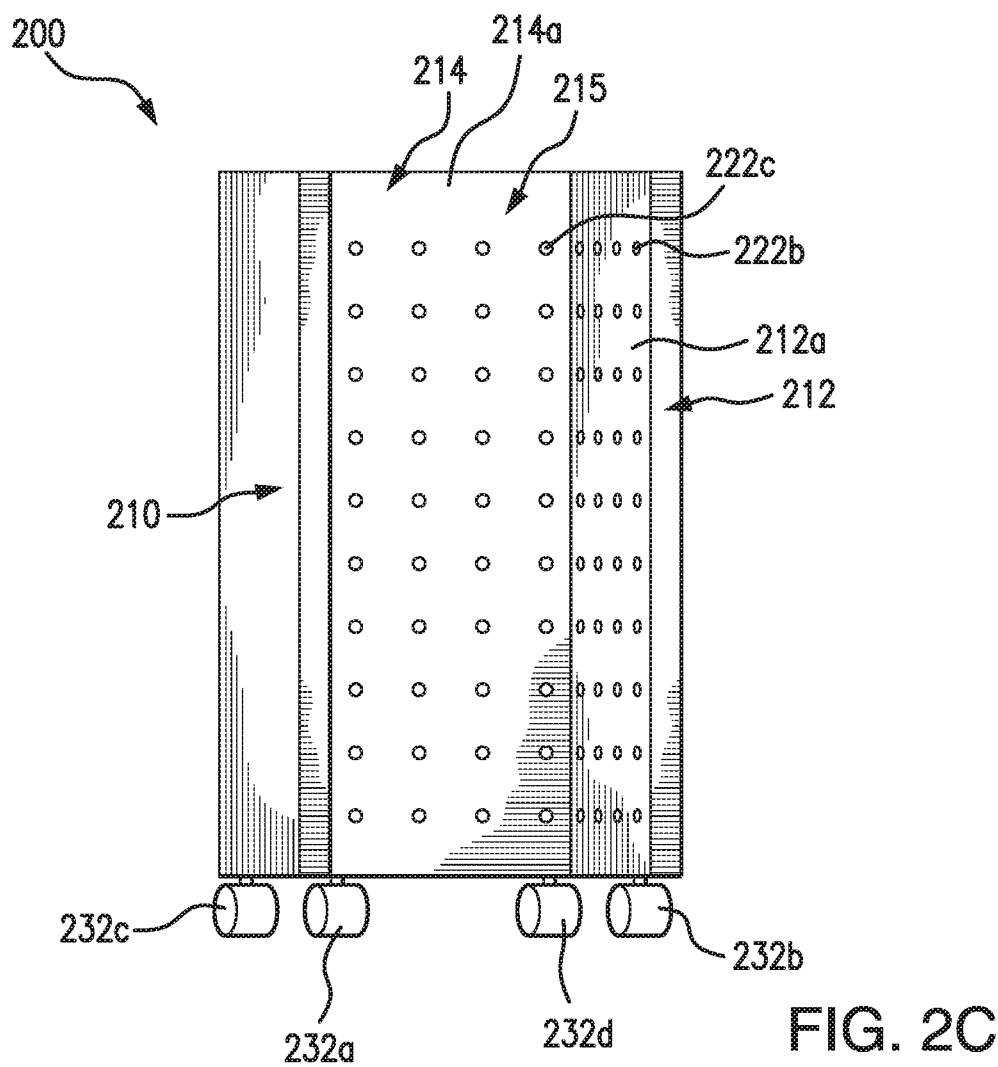
Figure 2D:
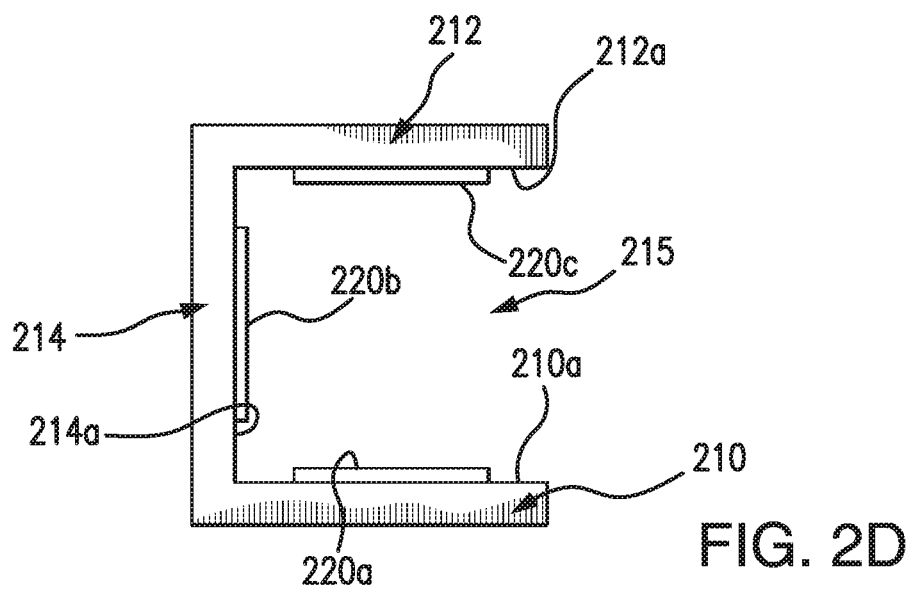
Figures 2E, 2F:
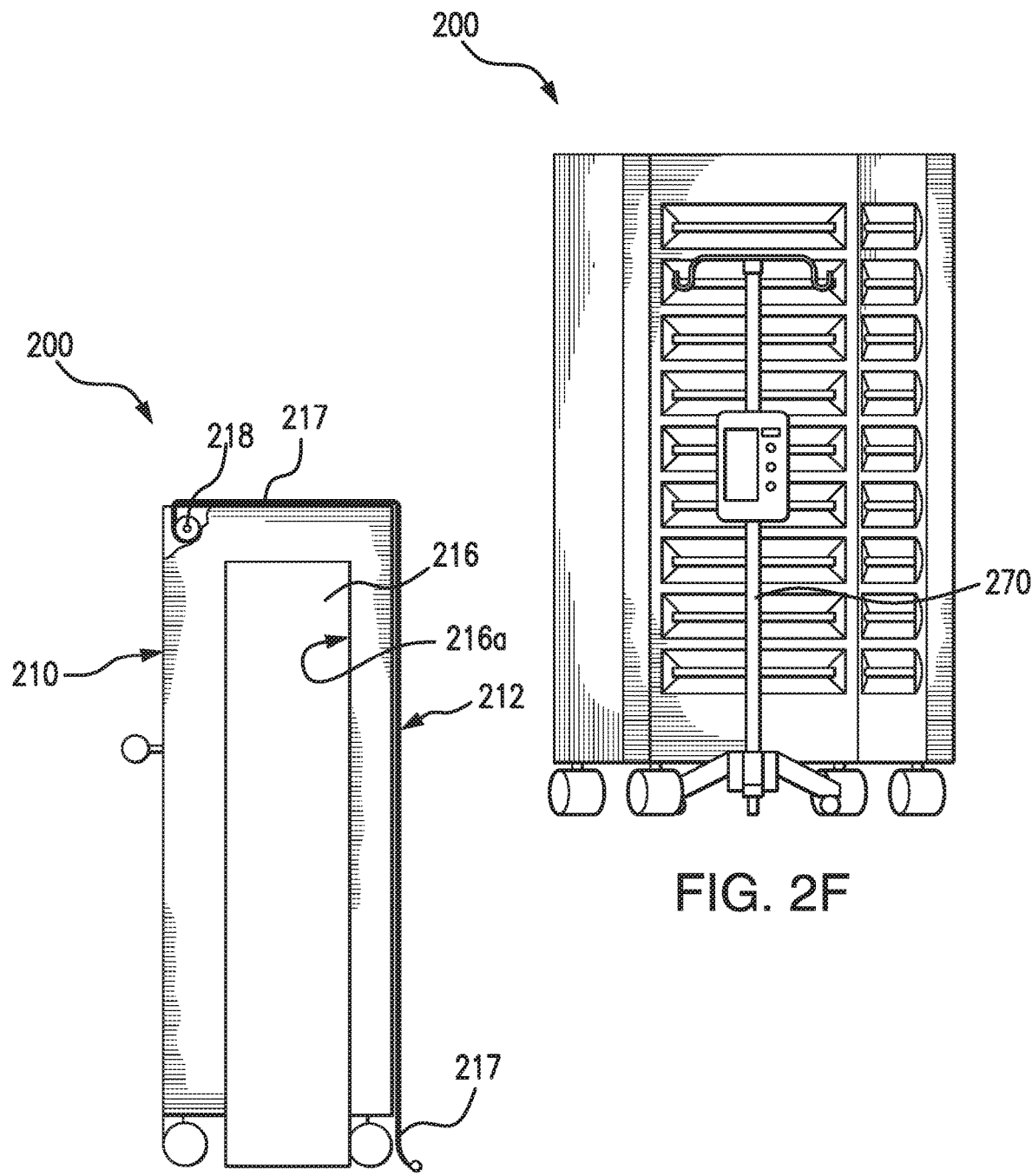

One or more pieces of equipment 270 may be introduced into the chamber 215 for a disinfection procedure (FIG. 2F). For example, a piece of equipment may be manually placed within the chamber (e.g., the IV pole shown in FIG. 2F). Alternatively, the chamber 215 may be manually or automatically advanced (e.g., rolled) around a piece of stationary equipment. With the piece of equipment positioned within the chamber, the front wall 219 or curtain 216 may be closed to seal or close the chamber and the disinfection procedure initiated. All commercially viable sizes are contemplated for the chamber 115. By way of non-limiting example, a chamber dimensioned to receive a standard sized intravenous pole may include an inner length of approximately 30 inches, an inner height of approximately 60 inches and an inner width of approximately 30 inches. In various embodiments, the size and dimensions of the opening and interior portion of the chamber may vary depending on the equipment to be disinfected.

In one embodiment, the rolling elements 232a-d may be configured to move between a first position in which the rolling elements extend beyond (e.g., below) the bottom portion of the first side wall 210, second side wall 212 and back wall 214, and a second position in which the rolling elements do not extend beyond the bottom portion of the first side wall 210, second side wall 212 and back wall 214. For example, the rolling elements may be attached to a piston and compressed gas source, as discussed above. With the rolling elements 232a-d in the first position (e.g., deployed or exposed), the disinfection system 200 may be manually or robotically moved (e.g., rolled). With the rolling elements 232a-d in the second position (e.g., retracted into a recess formed within the bottom portion of the first side wall, second side wall and back wall), the bottom portion of the first side wall 210, second side wall 212 and back wall 214 may be placed in contact with the floor underneath the disinfection system 200, thereby preventing energy from exiting the chamber and negating the associated risks from exposure to, e.g., UV energy. In various embodiments, the four-rolling element configuration depicted in FIGS. 2A-2C, 2E and 2F may allow the disinfection chamber to maneuver within and through the hallways and/or rooms of a hospital. However, the present disclosure is in no way limited to the configuration of rolling elements depicted herein, and may include any number of rolling elements arranged in various locations along the bottom portion of the first side wall 210, second side wall 212 and/or back wall 214.

In one embodiment, a disinfection system 100, 200 of the present disclosure may include a control panel 150, 250 on an outer surface of the first side wall, second side wall, front wall or back wall. The control panel 150, 250 may be configured to receive and process user input to control and/or monitor at least one function of the disinfection system 100, 200.

In various embodiments, the control panel 150, 250 may be configured to electrically communicate with one or more sensors on or within the chamber 115, 215. The one or more sensors may include a motion sensor configured to detect unintended motion in the vicinity of and/or within the chamber 115, 215. The one or more sensors may be configured to determine if the front wall of the chamber 115, 215 is closed, open or partially open (e.g., ajar). The one or more sensors may be configured to determine if a plane of the front wall is broken by, e.g., a piece of equipment within the chamber 115, 215. For example, the sensor may include a "laser curtain" that emits a beam of visible or invisible light across an opening of the chamber 115, 215 to detect an object that is impeding or blocking the opening. The control panel 150, 250 may be configured to alter a status of the disinfection system 100, 200 when any of the one or more sensors detect unintended motion, an open or partially open front wall and/or an impediment to an opening of the chamber. For example, the control panel 150, 25 may provide an audio alert (e.g., alarm), visual alert (e.g., flashing or blinking light) or electronic alert (e.g., message sent to a mobile device) to indicate the status of the chamber 115, 215 to a user of the disinfection system 100, 200. In addition, or alternatively, the control panel 150, 250 may automatically deactivate the disinfection system 100, 200 to stop the disinfection procedure if a user does not respond to the audio, visual or electronic alert within a predetermined time.

In various embodiments, the one or more sensors may include an electronic sensor, e.g., an electronic "nose", configured to detect, differentiate and/or quantify pathogens on or within the chamber 115, 215.

In various embodiments, the one or more sensors may include a UV light sensor configured to monitor the intensity or wavelength of UV energy within the chamber 115, 215. In addition, or alternatively, the UV light sensor may be configured to detect UV energy emitted (e.g., escaping or leaking) from the chamber 115, 215 (e.g., through a partially open front wall, etc.).

In various embodiments, the one or more sensors may include a camera to monitor and/or record the chamber 115, 215 during a disinfection procedure.

In various embodiments, the one or more sensors may include an include a radio frequency identification (RFID) sensor configured to identify a specific user of the disinfection system 100, 200. For example, the RFID sensor may recognize a RFID "badge" to allow access of specific personnel to the disinfection system 100, 200. In addition, or alternatively, the RFID sensor may recognize and RFID "tag" to identify and log a particular piece of equipment undergoing a disinfection procedure.

In various embodiments, the control panel 150, 250 may be configured to indicate a status of the disinfection system 100, 200. For example, the control panel 150, 250 may include a countdown clock indicating the time remaining on a disinfection procedure. The control panel 150, 250 may also include a real-time indicator of the intensity or wavelength of UV energy within the chamber 115, 215. The control panel may also include an indicator that regularly scheduled or emergency maintenance of the disinfection system 100, 200 is required.

In various embodiments, the control panel 150, 250 may include a power button with "on" and "off" settings to assist in preventing unauthorized use by cutting power to the chamber 115, 215 unless the power switch is in the "on" position.

In various embodiments, the control panel 150, 250 may be configured to electrically communicate with a reserve power source or battery to recharge the disinfection system 100, 200 in the event of power loss. The reserve power source may be integrated within the disinfection system 100, 200 or a component of a separate base station.

In various embodiments, the control panel 150, 250 may include an automated user interface, comprising on-board or remote control or access to the disinfection system 100, 200, a central processing unit (CPU), and non-transitory computer readable storage medium with computer executable code, which when executed by the CPU allows: processing and memory functionality to read, record, store, analyze, monitor, track, and control activity and safety features of the disinfection system 100, 200; user selected and automatic controls based on programmable settings and/or feedback from any of the sensors described herein; and internet network capability for access, monitoring and/or control of the disinfection system 100, 200 using, e.g., a tablet, phone, computer or application, among other administrative functions or operational functions of a system that may be automated, pre-set or pre-programmed.

Figure 6:
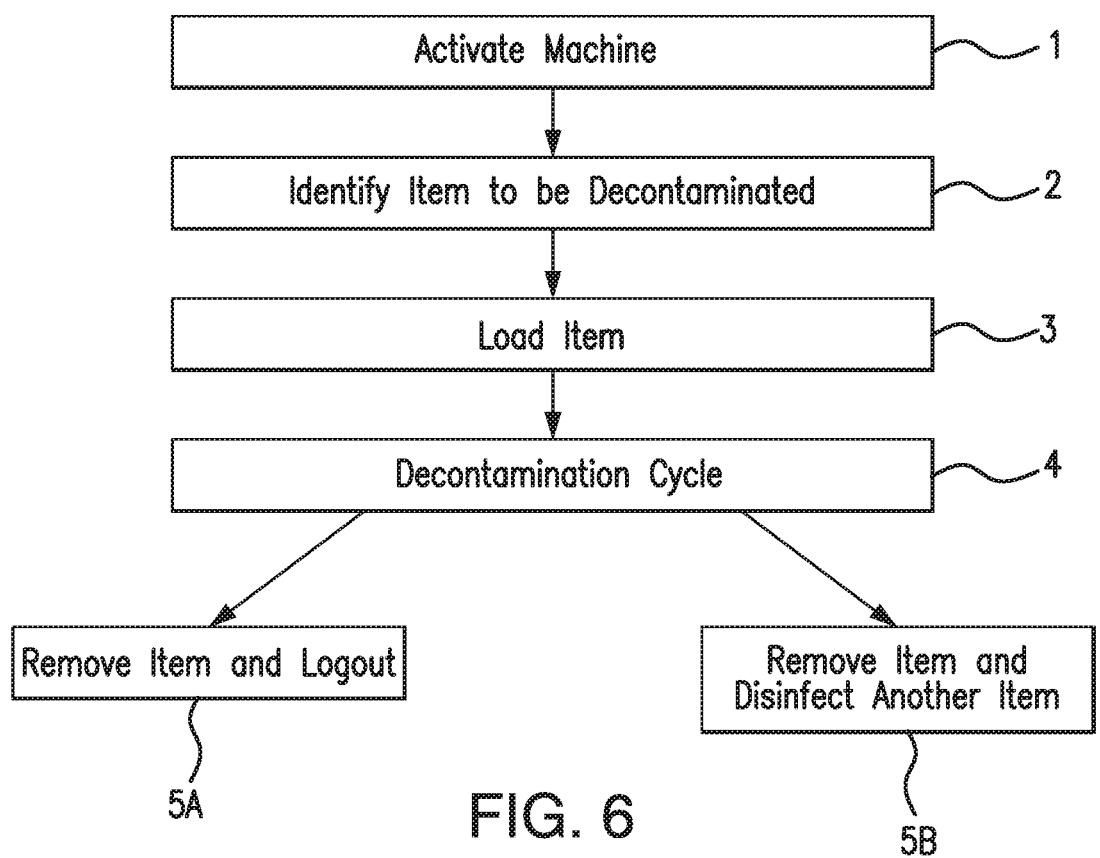
FIG. 6 depicts exemplary operational steps involved in using a disinfection system, according to one embodiment of the present disclosure.

Referring now to FIG. 6, a flow diagram of the basic operational steps involved in disinfecting a piece of equipment within a disinfection system (with reference as an example to systems 100, 200), according to embodiments of the present disclosure is shown. At step 1, the disinfection system 100, 200 may be activated using an access badge or entering an authorization number into the control panel 150, 250. At step 2, the equipment to be disinfected may be identified by scanning an identification tag on the equipment or entering an identification number into the control panel 150, 250. In step 3, the equipment to be disinfected may be placed within the chamber 115, 215 and the front wall or curtain closed. In step 4, the disinfection procedure may be initiated by pressing an "on" or "activation" button on the control panel 150, 250. The control panel 150, 250 may indicate the status of the disinfection procedure in real-time. In step 5A, once the disinfection procedure has ended, the front wall or curtain may be opened and the equipment removed from the disinfection chamber 115, 125. The front wall or curtain may then be closed and the disinfection system 100, 200 returned to a deactivate state by pressing an "off" or "logout" button on the control panel 150, 250. Alternatively, in step 5B, once the disinfection procedure has ended, the front wall or curtain may be opened and the equipment removed from the disinfection chamber 115, 215 and a second piece of equipment may then be loaded into the disinfection chamber 115, 215 and steps 1-4 repeated to perform another disinfection procedure.

Figure 7:
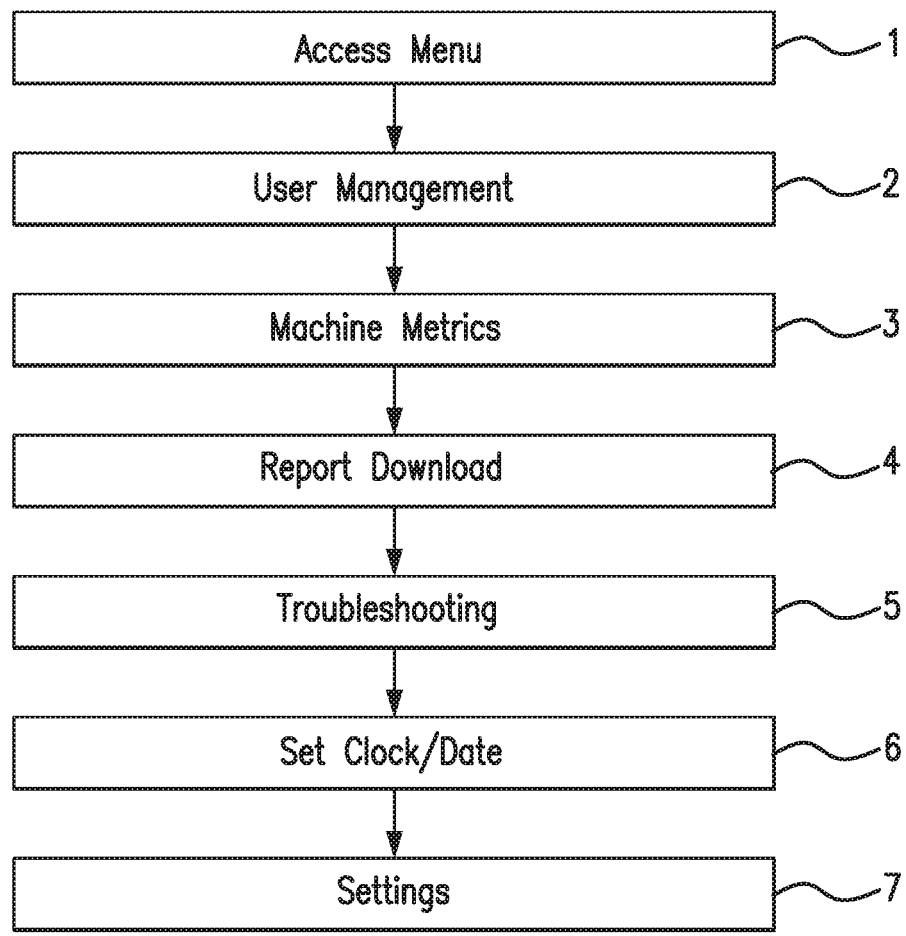
FIG. 7 depicts exemplary administrative functions involved in using a disinfection system, according to one embodiment of the present disclosure.

Referring to FIG. 7, a flow diagram of the basic administrative functions available on a control panel (with reference as an example to control panel 150, 250 of a disinfection system 100, 200), according to embodiments of the present disclosure is provided. At step 1, a user may select a variety of options from an access menu. A non-limiting example of such options may include "Machine Metrics," "Reports," "Troubleshooting," "User Management," "Set Clock/Date," "Settings," and "Home." At step 2, a user may be added to the disinfection system 100, 200 by pressing the "User Management" button. Relevant information about the new user may then be entered into the "User Management" screen, including, for example, the user's name, login number or RFID badge number. At step 3, a technician may review or monitor the status of the disinfection system 100, 200 by pressing the "Machine Metrics" button. The "Machine Metrics" screen may display the number of hours of use of each UV light source, the total number of disinfection procedures performed by the disinfection system 100, 200, the total number of hours of disinfection time performed by the disinfection system 100, 200 and the total number of door cycles (e.g., opening and closing) of the disinfection system 100, 200. At step 4, a user may download a report from the disinfection system 100, 200 by pressing the "Report" button and saving the selected information to a storage medium. At step 5, a technician may troubleshoot the disinfection system 100, 200 by pressing the "Troubleshoot" button and then reviewing the operational status of any of the sensors, UV lights, reflective units, doors, curtain or rolling elements discussed above. At step 5, a user may press the "Set Clock/Date" button and enter the appropriate year, month, week, day, hour, minute and second. At step 7, a technician may press the "Settings" button to set or change the parameters of a disinfection procedure. For example, the technician may enter a disinfection time of between 28-60 seconds. The technician may also increase or decreases the pass/fail threshold value of each UV sensor on or within the disinfection system 100, 200. The technician may also increase or decrease the intensity threshold of each UV light.

Figure 4A:
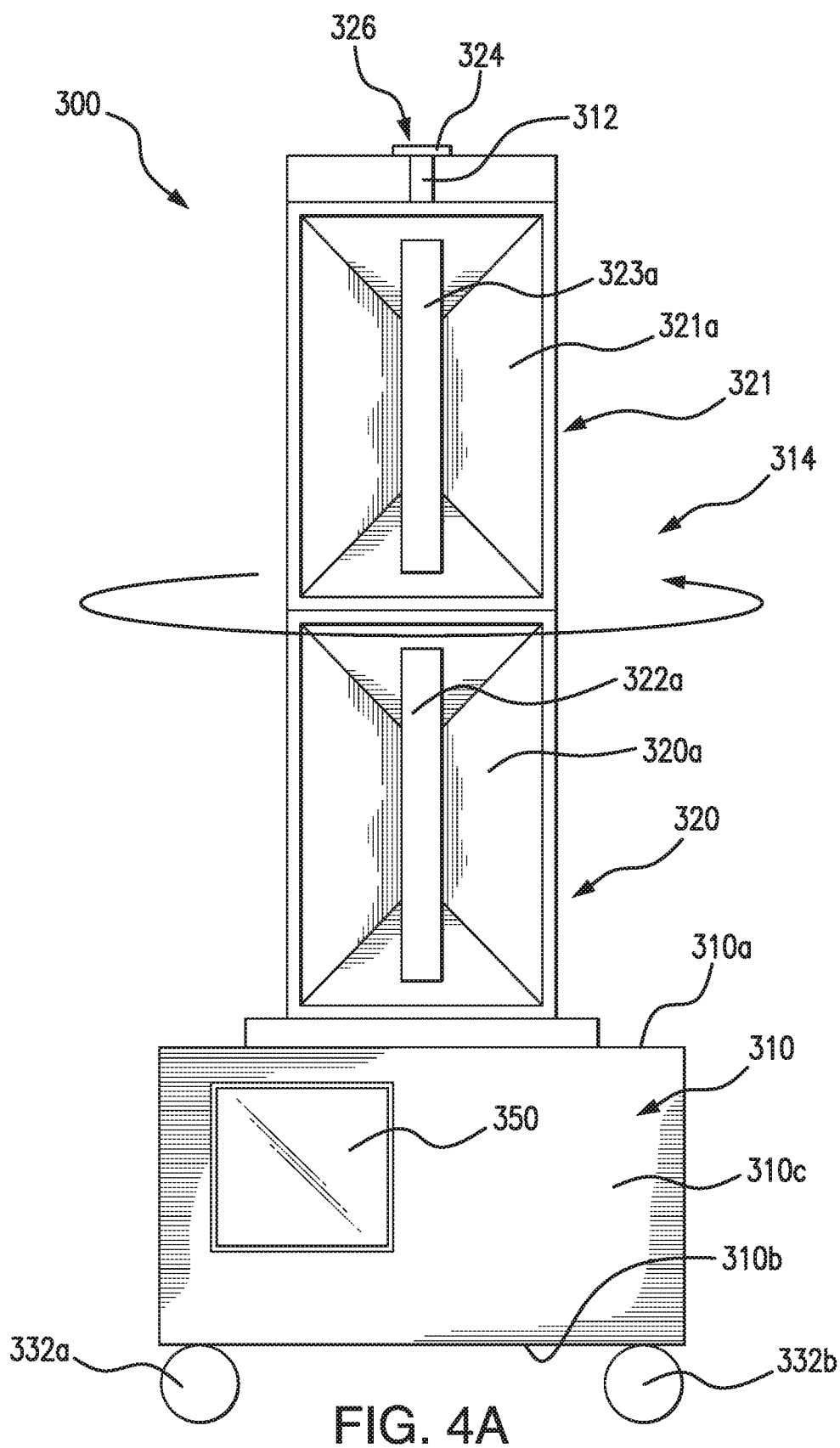
FIGS. 4A-4E provide perspective views of a disinfection system, according to one embodiment of the present disclosure.
Figure 4B:
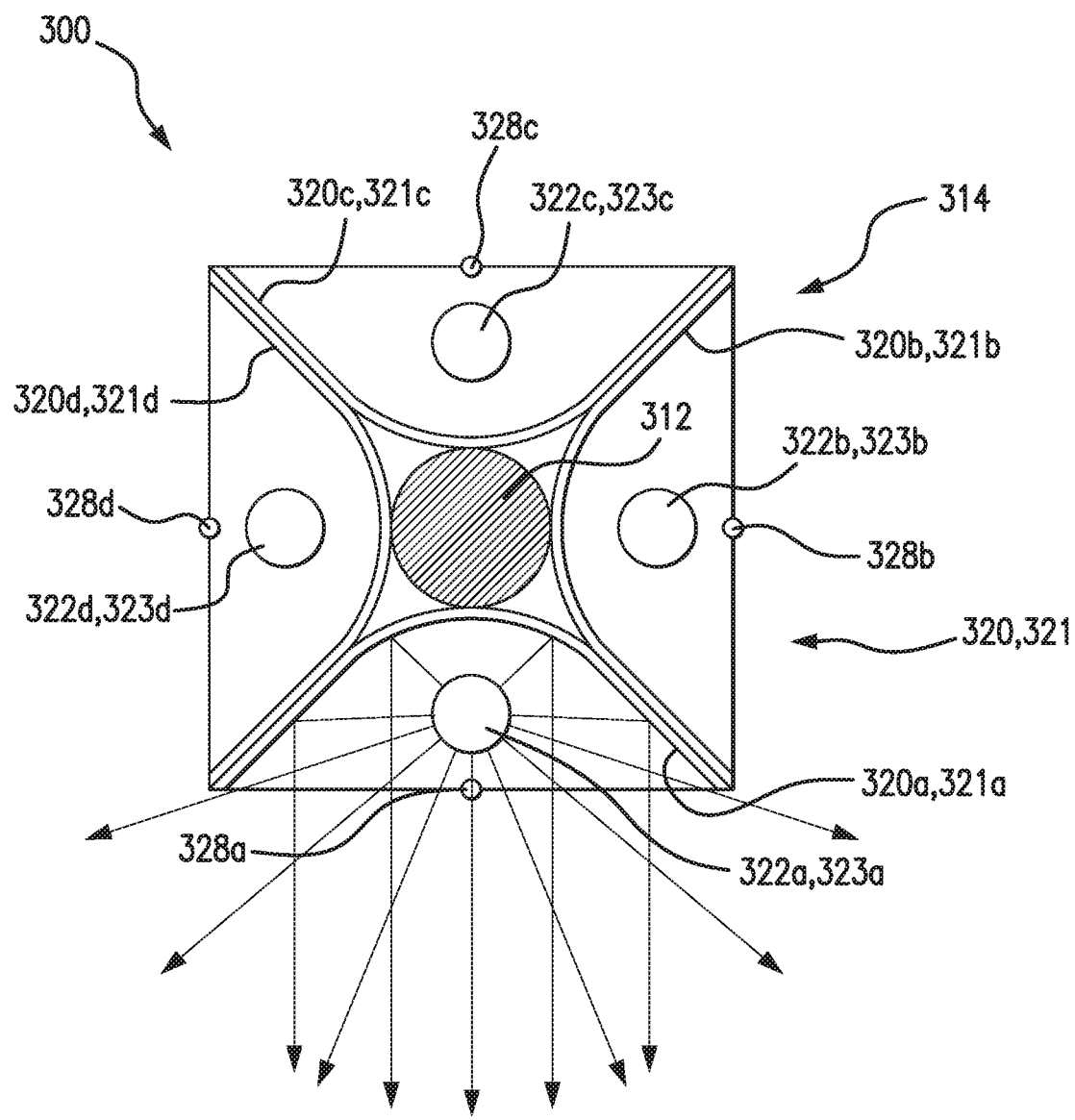
Figure 4C:
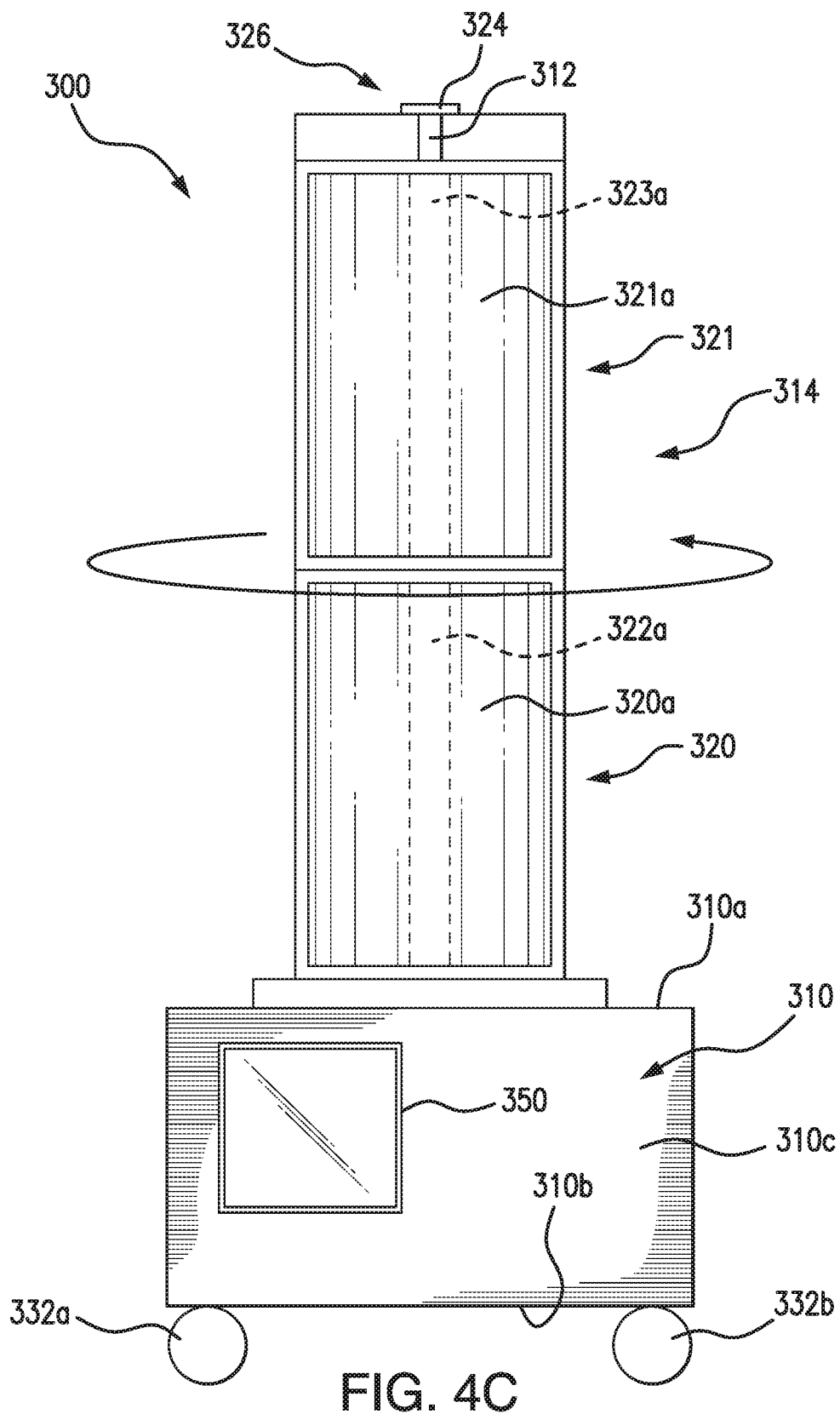

Referring to FIGS. 4A-4E, in one embodiment, a disinfection system 300 of the present disclosure may include a base 310 (e.g., platform, etc.) and a first stack of reflective units 320 rotatably attached (e.g., 360 degrees of rotation) to a top surface 310a of the base 310. A first array of energy sources 322 may be housed within the first stack of reflective units 320. A plurality of rolling elements 332a-332d (e.g., wheels, casters, sleds, etc.) may be attached to a bottom surface 310c of the base 310. In one embodiment, the first stack of reflective units 320 may be rotatably attached to the top surface 310a of the base 310 by a center shaft 312 that extends from the top surface 310a of the base 310 through a center portion of the first stack of reflective units 320. Alternatively, the top surface 310a of the base 310 may include a ball-bearing assembly, or other suitable rotating platform (not shown), configured to allow the first stack of reflective units 320 to rotate or pivot thereabout. The first stack of reflective units 320 may include a first reflective unit 320a, a second reflective unit 320b, a third reflective unit 320c and a fourth reflective unit 320d. In one embodiment, the first, second, third and fourth reflective units 320a-d may be arranged symmetrically around the center shaft 312, and include a substantially square cross-section (FIG. 4B). The first array of energy sources 322 may include a first energy source 322a removably or permanently disposed within the first reflective unit 320a, a second energy source 322b removably or permanently disposed within the second reflective unit 320b, a third energy source 322c removably or permanently disposed within the third reflective unit 320c and a fourth energy source 322d removably or permanently disposed within the fourth reflective unit 320d. In various embodiments, each of the first, second, third and fourth reflective units 320a-d may be oriented such that energy emitted from each respective first, second, third and fourth energy source 322a-d is directed outward from the first stack of reflective units 320, e.g., into a room or enclosure within which the disinfection system 300 is positioned.

Figure 4D:
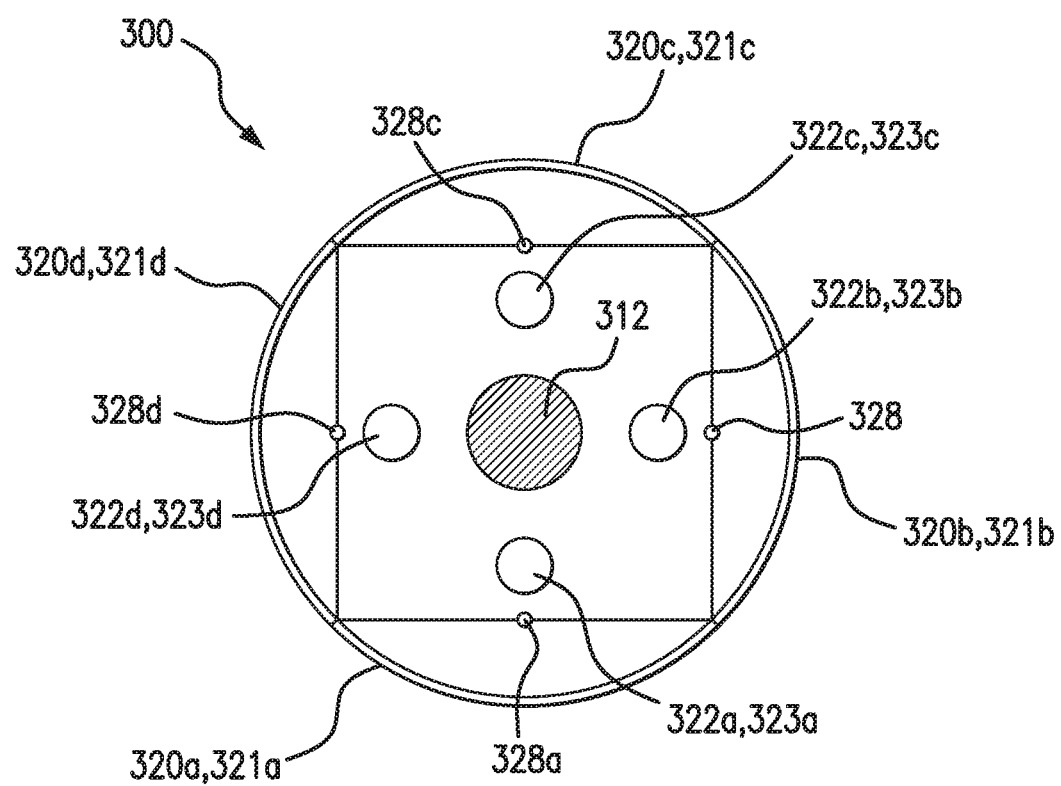
Figure 4E:
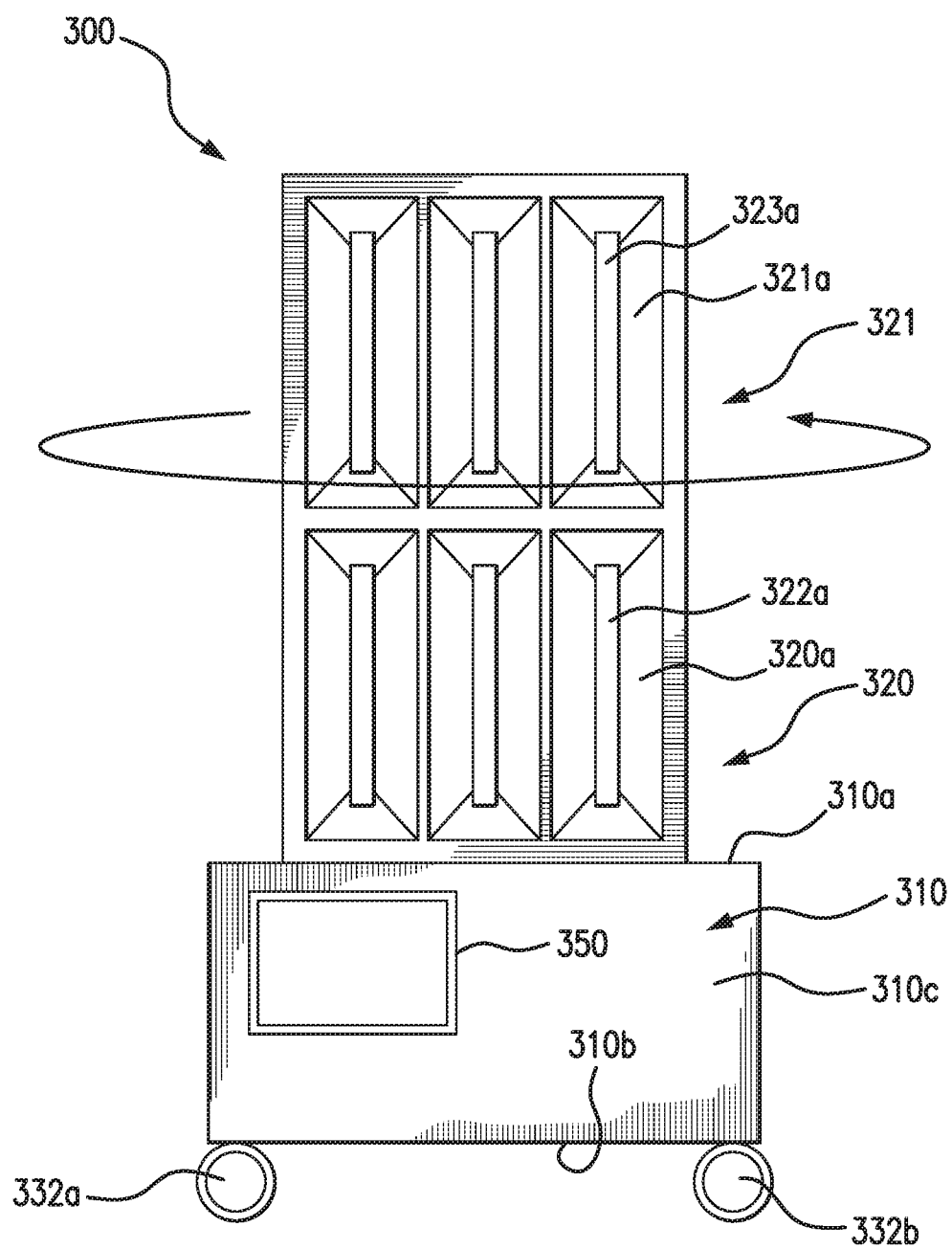

In one embodiment, each of the first, second, third and fourth reflective units 320a-d may be configured to rotate within the first stack of reflective units. For example, the first second, third and fourth reflective units 320a-d may be configured to rotate from a first position in which each reflective unit is disposed behind the respective first, second, third and fourth energy source 322a-d (FIG. 4B), to a second position in which each reflective unit is disposed in front of the respective first, second, third and fourth energy source 322a-d (FIG. 4D). In the first position, each of the first, second, third and fourth reflective units 320a-d may be configured to direct energy emitted from each of the first, second, third and fourth energy sources 322a-d away from the disinfection system 300, as discussed above. In the second position, each of the first, second, third and fourth reflective units 320a-d may be configured to block or shield energy emitted from each of the first, second, third and fourth energy sources 322a-d from exiting the first stack of reflective units 320. In addition, in the second position, each of the first, second, third and fourth reflective units 320a-d may be configured to protect each of the first, second, third and fourth energy sources 322a-d from damage, e.g., during movement and/or storage of the disinfection system 300. In one embodiment, the first, second, third and fourth reflective units 320a-d may rotate around the respective first, second, third and fourth energy source 322a-d (e.g., energy sources 322a-d remain stationary). In another embodiment, the first, second third and fourth reflective units 320a-d and the respective first, second, third and fourth energy sources (322a-d) may rotate together.

In one embodiment, the disinfection system 300 may further include a pivot point driver 324 extending through an inner portion of the center shaft 312. A top portion of the pivot point driver 324 may include first control arm 327a configured to contact an outer surface of the first reflective unit 320a at a first pivot point, a second control arm 327b configured to contact an outer surface of the second reflective unit 320b at a second pivot point, a third control arm 327c configured to contact an outer surface of the third reflective unit 320c at a third pivot point and a fourth control arm 327d configured to contact an outer surface of the fourth reflective unit 320d at a fourth pivot point. Each of the first, second, third and fourth reflective units 320a-d may be configured to individually rotate (e.g., between 180-360 degrees) about the respective first, second, third and fourth control arms 327a-d at the respective first, second, third or fourth pivot points. The rotation may be uniform, stepped or variable speed, and may be accomplished by various manual or automatic or motorized means, or the like.

In one embodiment, the disinfection system 300 may include a second array of energy sources 323 housed within a second stack of reflective units 321. The second stack of reflective units 321 may include a fifth reflective unit 321a, a sixth reflective unit 321b, a seventh reflective unit 321c and an eighth reflective unit 321d. The second array of energy sources 323 may include a fifth energy source 323a removably or permanently disposed within the fifth reflective unit 321a, a sixth energy source 323b removably or permanently disposed within the sixth reflective unit 321b, a seventh energy source 323c removably or permanently disposed within the seventh reflective unit 321c and an eighth energy source 323*d* removably or permanently disposed within the eighth reflective unit 321*d*. In various embodiments, each of the fifth, sixth, seventh and eighth reflective units 321*a-c* may be oriented such that energy emitted from each respective fifth, sixth, seventh and eighth energy source 323*a-d* is directed outward from the second stack of reflective units 321, e.g., into a room or enclosure within which the system 300 is positioned.

In one embodiment, each of the fifth, sixth, seventh and eighth reflective units 321*a-d* may be configured to rotate within the second stack of reflective units 321. For example, the fifth, sixth, seventh and eighth reflective units 321*a-d* may be configured to rotate from a first position in which each reflective unit is disposed behind the respective fifth, sixth, seventh and eighth energy source 323*a-d* (FIG. 4B), to a second position in which each reflective unit is disposed in front of the respective fifth, sixth, seventh and eighth energy source 323*a-d* (FIG. 4D). In the first position, each of the fifth, sixth, seventh and eighth reflective units 321*a-d* may be configured to direct energy emitted from each of the fifth, sixth, seventh and eighth energy sources 323*a-d* away from the disinfection system 300, as discussed above. In the second position, each of the fifth, sixth, seventh and eighth reflective units 321*a-d* may be configured to block or shield energy emitted from each of the fifth, sixth, seventh and eighth energy sources 323*a-d* from exiting the second stack of reflective units 321. In addition, in the second position, each of the fifth, sixth, seventh and eighth reflective units 321*a-d* may be configured to protect each of the fifth, sixth, seventh and eighth energy sources 323*a-d* from damage, e.g., during movement and/or storage of the disinfection system 300. In one embodiment, the fifth, sixth, seventh and eighth reflective units 321*a-d* may rotate around the respective fifth, sixth, seventh and eighth energy source 323*a-d* (e.g., energy sources 323*a-d* remain stationary). In another embodiment, the fifth, sixth, seventh and eighth reflective units 321*a-d* and the respective fifth, sixth, seventh and eighth energy sources (323*a-d*) may rotate together.

In one embodiment, the second stack of reflective units 321 may be disposed on top of the first stack of reflective units 320 such that the center shaft 312 extends from the top surface 310*a* of the base 310 through a center portion of the first and second stacks of reflective units 320, 321. The fifth, sixth, seventh and eighth reflective units 321*a-d* may be arranged symmetrically around the center shaft 312 and include a substantially square cross-section (FIG. 4B). In one embodiment, the first and second stacks of reflective units 320, 321 may rotate about the center shaft 312 in the same direction (e.g., the first and second stacks of reflective units both rotate clockwise, or the first and second stacks of reflective units both rotate counterclockwise). In another embodiment, the first and second stacks of reflective units 320, 321 may rotate in opposite directions about the center shaft 312 ((e.g., the first stack of reflective units rotates clockwise and the second stack of reflective units rotates counterclockwise). Alternatively, the first stack of reflective units 320 may be disposed alongside the second stack of reflective units 321, e.g., in a side-by-side configuration (not shown). A speed of rotation of the stacks may be selected and controlled to provide a particular application and/or intensity level of UV light with respect to an object or area being treated. For example, in various applications, given a certain proximity of the stacks to the object or space, a rotation of 1-4 revolutions per minute would be suitable like the first stack, the rotation of the second stack may be uniform, stepped or variable speed, and may be accomplished by various manual or automatic or motorized means, or the like.

A speed of rotation of the stacks may be selected and controlled to provide a particular application and/or intensity level of UV light with respect to an object or area being treated. For example, in various applications, given a certain proximity of the stacks to the object or area, a rotation of 1-4 revolutions per minute would be suitable. The speeds of rotation of the first stack relative to the second stack may be the same or different.

In various embodiments, each of the reflective units 320*a-d*, and 321*a-d* may be independently adjustable within the respective first or second stack of reflective units 320, 321 such that the direction or angle of the reflective unit may be adjusted, e.g., manually or automatically. In one embodiment, each of the reflective units 320*a-d* and 321*a-d* may define or include a substantially concave shape such that energy emitted from each of the respective energy source 322*a-d* and 323*a-d* is directed or focused away from the disinfection system 300. By way of non-limiting example, each of the reflective units 320*a-d* and 321*a-d* may include a back section, and at least three reflective sections, each of which may be disposed off normal with respect to the back section. This configuration of reflective sections may allow energy emitted from the energy sources to be directed in every direction into an enclosure rather than only up and down or left and right. In this manner, disinfecting energy may be directed onto multiple surfaces (e.g., equipment, desks, walls, floor ceiling, doors, door knobs, handles, railings, etc.) within an enclosure in which the disinfection system 300 is positioned. In various embodiments, each of the reflective units 320*a-d* and 321*a-d* (including the reflective surfaces) may comprise one or more commercially suitable materials, including, for example, mirrors, powder-coated and other metal sheets, and Pebbletone™ and Hammertone™ finishes.

In various embodiments, each of energy sources 322*a-d* and 323*a-d* may be configured to emit ultraviolet (UV) light. For example, each energy source may include mercury vapor bulbs or tubes, xenon gas bulbs or tubes, light emitting diodes (LED), light emitting nanoparticles, or any other energy source configured to emit ultraviolet (UV) light at a wavelength of approximately 320-400 nm (e.g., UV-A), approximately 290-320 nm (e.g., UV-B) and/or approximately 200-280 nm (e.g., UV-C). Each of the energy sources 322*a-d* and 323*a-d* may include dual UV emitting bulbs, although the number of bulbs may be varied. Although the UV emitting bulbs are depicted as elongate bulbs, other suitable UV emitting sources may include, by way of non-limiting example, a 36 Watt bulb that emits UV light at a wavelength of approximately 254 nm.

Although any of the UV-A, UV-B, or UV-C wavelengths of energy may provide sufficient disinfection of equipment within the chamber, in one embodiment an energy source configured to emit at least 30 watts of UV energy, at least 75% of which is UV-C energy, may provide an optimal disinfection intensity. In addition, or alternatively, the UV energy emitting source may include a light emitting diode (LED) and/or light emitting nanoparticles deposited or grown on a flexible metallic surface, as such components and processes for producing such components are known in the art.

Figure 5:
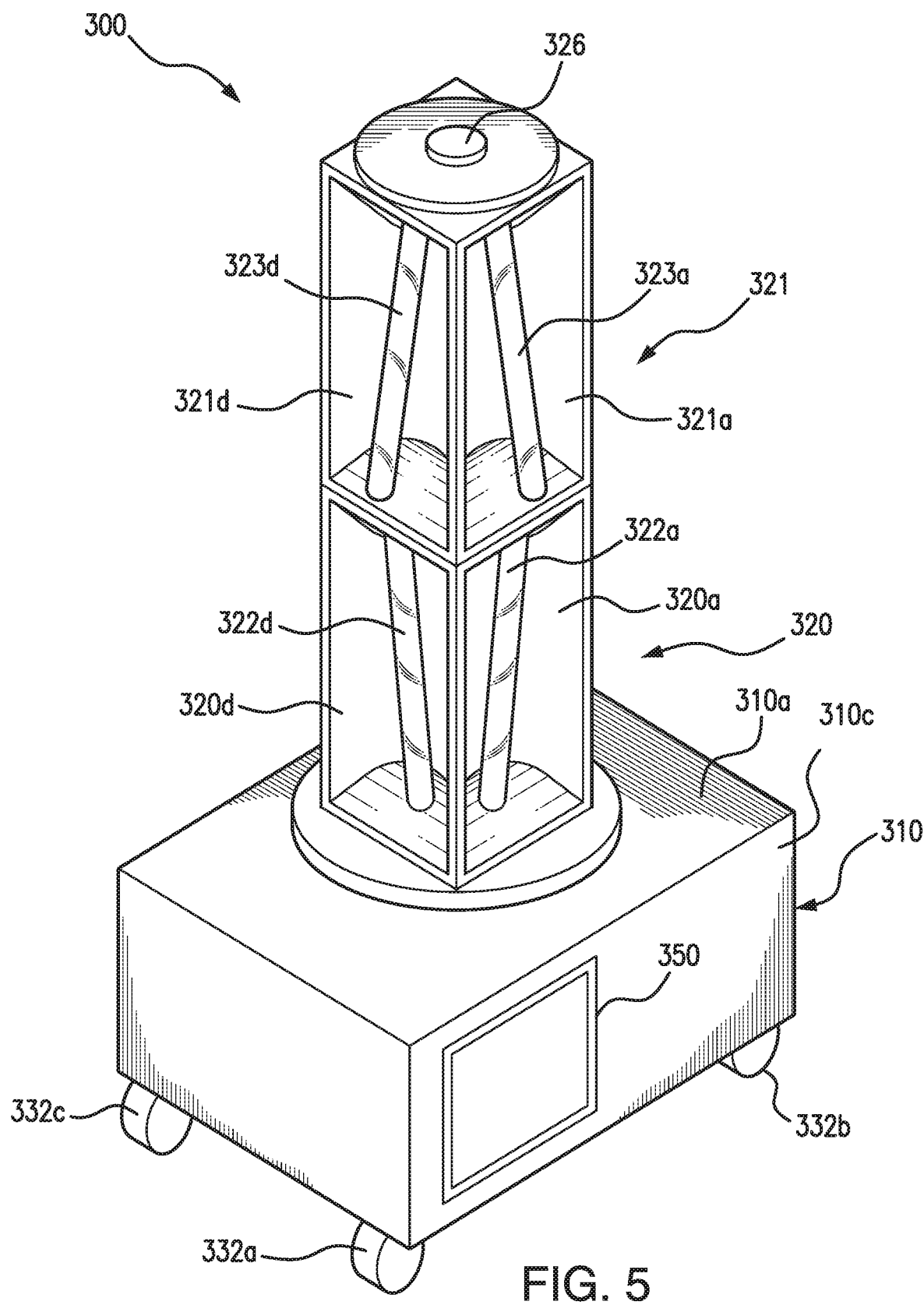
FIG. 5 provides a perspective view of a disinfection system, according to one embodiment of the present disclosure.

The present disclosure is in no way limited to the number and/or arrangement of stacks of reflective units and/or energy sources (such as depicted in FIG. 4A), and may include reflective units and energy sources disposed in any suitable location, orientation, configuration, size and/or number (such as on top of the base 310, including, for example the first and second stacks of reflective units arranged in tandem (FIG. 4E)). Referring to FIG. 5, in one embodiment, any or all of the energy sources 322*a-d* and/or 323*a-d* may be disposed within the respective reflective unit 320*a-d* and/or 321*a-d* at an angle to preferentially direct energy towards the floor and/or ceiling of an enclosure to disinfects otherwise hidden or obscured objects or surfaces within the enclosure. Such orientation may be applied with the reflective units of any of the various embodiments discussed above.

In one embodiment, the base 310 may be robotic and configured to move autonomously to a series of pre-determined, mapped, acquired or learned waypoints to perform separate and sequential disinfection procedures within an enclosure. For example, the robotic base may move to a first waypoint within an enclosure and activate the first and/or second arrays of energy sources 322, 323 for a sufficient amount of time (e.g., five minutes) to disinfect a first region of the enclosure. The robotic base may then move to a second waypoint and re-activate the first and/or second arrays of energy sources 322, 323 to disinfect a second region of the enclosure, and then move to a third waypoint and re-activate the first and/or second arrays of energy sources 322, 323 to disinfect a third region of the enclosure. Alternatively, the first and/or second energy sources 322, 323 may remain activated as the robotic base moves between waypoints to further disinfect the enclosure. The first and/or second stacks of reflective units 320, 321 may rotate about the robotic base 310 at any or all of these waypoints (or while moving between waypoints) to emit energy with the proper intensity, proximity and line of sight to disinfect equipment and/or surfaces within the enclosure. In addition, or alternatively, one or more of the reflective units 320*a*-320*d* and/or 321*a*-321*d*, may tilt or rotate within the respective first or second stack of reflective units 320, 321 to emit energy at various angles to disinfect otherwise obscured surfaces that might harbor pathogens.

Although the disinfecting system 300 of the present disclosure generally includes a robotic base with first and/or second stacks of reflective units and arrays of energy sources rotatably disposed thereon, in various embodiments the base may be non-robotic, e.g., requiring a user to manually roll the base to the desired position within an enclosure to perform a disinfection procedure. In addition, or alternatively, the base may be robotic and the first and/or second stacks of reflective units and arrays of energy sources may be non-rotatably disposed thereon.

In one embodiment, a disinfection system 300 of the present disclosure may include a control panel 350 on an outer surface of the base 310. The control panel 350 may be configured to receive and process user input to control and/or monitor at least one function of the disinfection system 300. The control 350 may be configured to electrically communicate with one or more sensors on or within the base 310 and/or first or second stacks of reflective units 320, 321.

In various embodiments, the one or more sensors may include a motion sensor. The motion sensor may be configured to detect unintended motion in the vicinity of the disinfection system 300. In various embodiments, the one or more sensors may be configured to determine if a person that might be harmed by UV light is present within the enclosure before or during a disinfection procedure. The one or more sensors may be configured to detect stationary objects within the enclosure such that the disinfection system 300 is able to robotically navigate around such objects. The control panel 350 may be configured to alter a status of the disinfection procedure when the one or more sensor detects such unintended motion within the enclosure. For example, the control panel 350 may provide an audio alert (e.g., alarm), visual alert (e.g., flashing or blinking light) or electronic alert (e.g., message sent to a mobile device) to indicate the presence of the disinfection system 300 to the user within the enclosure. In addition, or alternatively, the control panel 350 may automatically deactivate the disinfection system 300 to stop the disinfection procedure if a user does not respond to the audio, visual or electronic alert within a predetermined time.

In various embodiments, the one or more sensors may include an electronic sensor, e.g., an electronic "nose", configured to detect, differentiate and/or quantify pathogens on or within the enclosure.

In various embodiments, the one or more sensors may include a UV light sensor configured to monitor the intensity or wavelength of UV energy emitted from the disinfection system 300.

In various embodiments, the one or more sensors may include a camera to monitor and/or record the disinfection system 300 and/or enclosure during a disinfection procedure.

In various embodiments, the one or more sensors may include an include a radio frequency identification (RFID) sensor configured to identify a specific user of the disinfection system 300. For example, An RFID sensor may be included on either or both of the interior or exterior of the disinfection system 300. For example, an authorized user, with proper badge access, may swipe the RFID sensor and be permitted access to the control panel display in order to activate the system. An RFID sensor may also be included on the disinfection system 300, e.g., to identify a badge associated with a particular enclosure that is subject to repeated disinfecting cycles. Reading the badge on a specific enclosure (e.g., a door to the enclosure) may allow for identification and logging of the enclosure, and may be associated with a pre-programmed activation cycle specific to the enclosure and/or equipment inside the enclosure. The RFID sensor may also act as a failsafe, protecting against activation unless the RFID sensor picks up the presence of a badge identifying the specific enclosure and indicating that a disinfection protocol is scheduled to be performed.

In various embodiments, the control panel 350 may be configured to provide an indicator or a status of the disinfection system 300. For example, the control panel 350 may include a countdown clock indicating the time remaining on a disinfection procedure. The countdown clock may be wirelessly transmitted to a user outside of the enclosure to monitor the status of a disinfection procedure. The control panel 350 may also wirelessly transmit a real-time indicator of the intensity or wavelength of UV emitted from the disinfection system 300. The control panel 350 may also include an indicator that regularly scheduled or emergency maintenance of the disinfection system 300 is required.

In various embodiments, the control panel 350 may include a power button with "on" and "off" settings to assist in preventing unauthorized use by cutting power to the disinfection system 300 unless the power switch is in the "on" position.

In various embodiments, the control panel 350 may be configured to electrically communicate with a reserve power source or battery to recharge the disinfection system 300 in the event of power loss. The reserve power source may be integrated within the disinfection system 300 or a component of a separate base station.

In various embodiments, the control panel 350 may be include an automated user interface, comprising on-board or remote control or access to the disinfection system 300, a CPU, and non-transitory computer readable storage medium with computer executable code, which when executed by the CPU allows: processing and memory functionality to read, record, store, analyze, monitor, track, and control activity and safety features of the disinfection system 300; user selected and automatic controls based on programmable settings and/or feedback from any of the sensors described herein; and internet network capability for access, monitoring and/or control of the disinfection system 300 using, e.g., a tablet, phone, computer or application, among other administrative functions or operational functions of a system that may be automated, pre-set or pre-programmed. Any of the sensor and/or robotic functions described above may be computer automated, e.g., without user input or after certain user input is provided, and may be programmed into the CPU as executable instructions carried out automatically with respect to activation, set-up, maintenance, movement and/or monitoring of the disinfection system 300. In addition, any of the operational steps described above (e.g., FIGS. 6-7) may be similarly computer automated, including functions related to rotation, direction and/or orientation of the reflective units or energy sources on the optionally robotic base. For example, programmable rotation may be a function of UV light intensity levels determined by one or more sensors, such that rotation speeds up or slows down based on a proximity of the disinfection system 300 to a specific piece of equipment within an enclosure and/or the time spent performing a disinfection procedure at a given waypoint.

All of the systems and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An apparatus, comprising:
a plurality of walls defining a chamber, the plurality of walls including a bottom wall, a first side wall, a second side wall, a top wall, and a back wall;
a sensor configured to identify a user to provide the user access to the chamber;
a plurality of reflective units, each reflective unit from the plurality of reflective units including a concave surface facing into the chamber, the plurality of reflective units including a set of reflective units disposed on an inner surface of each of the first side wall, the second side wall, the top wall, and the back wall, the set of reflective units disposed on each of the first side wall and the second side wall covering a majority of that side wall and including at least one reflective unit extending to a height of the bottom wall; and
a plurality of energy sources configured to emit electromagnetic energy, the plurality of energy sources including an energy source housed within each reflective unit disposed on the inner surface of each of the first side wall, the second side wall, the top wall, and the back wall,
the concave surface of each reflective unit from the plurality of reflective units configured to direct the electromagnetic energy emitted by the plurality of energy sources toward an object disposed in the chamber such that the electromagnetic energy disinfects an exterior surface of the object.

2. The apparatus of claim 1, wherein the electromagnetic energy is UV-C.

3. The apparatus of claim 1, wherein the plurality of energy sources are configured to emit the electromagnetic energy at an intensity of at least 100 μW/cm$^2$ at 1 meter.

4. The apparatus of claim 1, wherein the chamber includes an inner height, an inner width, and an inner length of at least approximately 36 inches.

5. The apparatus of claim 1, wherein the plurality of walls further define an opening to the chamber, the chamber and the opening being sized to receive at least one of: a gurney, a wheelchair, or an intravenous (IV) pole.

6. The apparatus of claim 1, wherein each of the first side wall, the second side wall, the top wall, and the back wall include a removable panel configured to be removed from the respective wall to enable access to at least one reflective unit from the plurality of reflective units or at least one energy source from the plurality of energy sources.

7. The apparatus of claim 1, further comprising a front wall movable between (1) an open configuration to provide an opening to the chamber and (2) a closed configuration to seal the chamber and block the electromagnetic energy emitted by the plurality of energy sources from exiting the chamber.

8. The apparatus of claim 7, wherein the front wall includes a reflective surface configured to reflect the electromagnetic energy emitted by the plurality of energy sources into the chamber.

9. The apparatus of claim 7, wherein the front wall is connected to the first side wall or the second side wall by at least one hinge.

10. The apparatus of claim 1, wherein the bottom wall includes a conveyor system configured to move the object into and out of the chamber.

11. The apparatus of claim 1, wherein the sensor is a first sensor, and further comprising one or more second sensors disposed near or within the chamber, the one or more second sensors including at least one of:
an electronic sensor configured to at least one of detect, differentiate, or quantify a pathogen on or within the chamber; or
a light sensor configured to monitor at least one of an intensity or wavelength of the electromagnetic energy emitted by the plurality of energy sources.

12. The apparatus of claim 1, wherein the sensor is a first sensor, and further comprising a processor operatively coupled to a user interface and a second sensor, the processor configured to:
receive at least one of an input from the user interface or feedback from the second sensor; and
control an operation of at least one energy source from the plurality of energy sources based on the at least of the input or the feedback.

13. An apparatus, comprising:
a plurality of walls defining a chamber, the plurality of walls including a bottom wall and a plurality of side walls;

a first sensor configured to identify a user to provide the user access to the chamber;

a plurality of reflective units including a set of reflective units disposed on an inner surface of each side wall from the plurality of side walls, the set of reflective units disposed on each side wall from the plurality of side walls covering a majority of that side wall and including at least one reflective unit extending to a height of the bottom wall;

a plurality of energy sources configured to emit electromagnetic energy, the plurality of energy sources including an energy source housed within each reflective unit from the plurality of reflective units such that the plurality of reflective units can direct the electromagnetic energy emitted by the plurality of energy sources toward an object disposed in the chamber to disinfect an exterior surface of the object;

at least one second sensor configured to monitor a condition of at least one of: the plurality of walls, the plurality of reflective units, the plurality of energy sources, an environment near or within the chamber, or the object; and a control unit configured to:
control an operation of the plurality of energy sources; and
present, in response to receiving information indicative of the condition from the at least one second sensor, a message to the user based on the information.

14. The apparatus of claim 13, wherein the control unit is further configured to:
determine that there is motion within the chamber based on the information received from the at least one second sensor,
the control unit configured to control the operation of the plurality of energy sources by deactivating the plurality of energy sources in response to determining that there is motion within the chamber.

15. The apparatus of claim 14, wherein the message is an alert indicating that there is motion within the chamber.

16. The apparatus of claim 13, wherein the control unit is further configured to present information indicative of a status of a disinfection procedure of the object.

17. The apparatus of claim 13, wherein the first sensor is further configured to read a radio frequency identification (RFID) tag associated with the object being disinfected, the control unit further configured to control the operation of the at least one energy source based on information provided by the RFID tag.

18. An apparatus, comprising:
a plurality of walls defining a chamber, the plurality of walls including a bottom wall and a plurality of side walls;
a sensor configured to identify a user to provide the user access to the chamber;
a plurality of reflective units including a set of reflective units disposed on an inner surface of each side wall from the plurality of side walls, the set of reflective units disposed on each side wall from the plurality of side walls covering a majority of that side wall and including at least one reflective unit extending to a height of the bottom wall;
a plurality of energy sources configured to emit electromagnetic energy, the plurality of energy sources including an energy source housed within each reflective unit from the plurality of reflective units such that the plurality of reflective units can direct the electromagnetic energy emitted by the plurality of energy sources toward an object disposed in the chamber to disinfect an exterior surface of the object; and
a control unit configured to:
activate, after the user has been provided access to the chamber, the plurality of energy sources to initiate a disinfection procedure of the object;
present information indicative of a status of the disinfection procedure during the disinfection procedure; and
communicate information associated with at least one of the user, the object, or the disinfection procedure to a compute device remote from the control unit.

19. The apparatus of claim 18, wherein the control unit is further configured to:
receive an input from the user that specifies one or more parameters of the disinfection procedure; and
control an operation of the plurality of energy sources based on the input.

20. The apparatus of claim 1, wherein the set of reflective units disposed on each of the first side wall and the second side wall are adjacent to and arranged substantially parallel to one another.

21. The apparatus of claim 1, wherein the bottom wall includes a reflective surface configured to reflect the electromagnetic energy emitted by the plurality of energy sources into the chamber.

* * * * *